United States Patent
Chen et al.

(10) Patent No.: US 11,666,556 B2
(45) Date of Patent: Jun. 6, 2023

(54) PHARMACEUTICAL COMBINATION, COMPOSITION AND COMPOUND PREPARATION CONTAINING GLUCOKINASE ACTIVATOR AND K-ATP CHANNEL BLOCKER, PREPARATION METHOD THEREFOR AND USE THEREOF

(71) Applicant: HUA Medicine (Shanghai) Ltd., Shanghai (CN)

(72) Inventors: Li Chen, Shanghai (CN); Yongguo Li, Shanghai (CN); Gaosen Wang, Shanghai (CN); Huisheng Gao, Shanghai (CN)

(73) Assignee: HUA MEDICINE (SHANGHAI) LIMITED, Shanghai (CN)

( * ) Notice: Subject to any disclaimer, the term of this patent is extended or adjusted under 35 U.S.C. 154(b) by 152 days.

(21) Appl. No.: 17/058,863

(22) PCT Filed: May 28, 2019

(86) PCT No.: PCT/CN2019/088862
§ 371 (c)(1),
(2) Date: Nov. 25, 2020

(87) PCT Pub. No.: WO2019/228363
PCT Pub. Date: Dec. 5, 2019

(65) Prior Publication Data
US 2021/0220334 A1 Jul. 22, 2021

(30) Foreign Application Priority Data
May 31, 2018 (CN) .......................... 201810556685.6

(51) Int. Cl.
*A61K 31/4155* (2006.01)
*A61K 9/20* (2006.01)
(Continued)

(52) U.S. Cl.
CPC ........ *A61K 31/4155* (2013.01); *A61K 9/1611* (2013.01); *A61K 9/1617* (2013.01);
(Continued)

(58) Field of Classification Search
CPC .............. A61K 31/4155; A61K 9/1611; A61K 9/1617; A61K 9/1635; A61K 9/1694;
(Continued)

(56) References Cited

U.S. PATENT DOCUMENTS 5,985,326 A * 11/1999 Butler .................. A61K 31/551 424/487
2008/0107725 A1* 5/2008 Albano .................. A61K 47/32 514/255.06

(Continued)

FOREIGN PATENT DOCUMENTS

| CN | 106474480 A | 3/2017 |
| CN | 107854435 A | 3/2018 |

(Continued)

OTHER PUBLICATIONS

Research J Pharm and Tech 5:190-197, 2012 (Year: 2012).*

(Continued)

*Primary Examiner* — Savitha M Rao
(74) *Attorney, Agent, or Firm* — Jones Day

(57) ABSTRACT

The present invention relates to a pharmaceutical combination, the pharmaceutical combination comprising a glucokinase activator or a pharmaceutically acceptable salt thereof, an isotopic label thereof, a crystal form thereof, a hydrate, a solvate, a diastereomer or enantiomer, and a K-ATP channel blocker. The present invention further relates to a pharmaceutical composition, a fixed dose compound preparation, and a method for preparing the pharmaceutical composition and the fixed dose compound preparation as well as a use thereof.

23 Claims, 1 Drawing Sheet

(51) Int. Cl.
| | |
|---|---|
| A61K 9/28 | (2006.01) |
| A61K 31/155 | (2006.01) |
| A61P 3/10 | (2006.01) |
| A61K 9/16 | (2006.01) |
| A61K 31/40 | (2006.01) |
| A61K 31/403 | (2006.01) |
| A61K 31/4985 | (2006.01) |
| A61K 31/522 | (2006.01) |
| A61K 31/4035 | (2006.01) |
| A61K 31/4439 | (2006.01) |
| A61K 31/7034 | (2006.01) |
| C07D 403/12 | (2006.01) |
| A61K 47/38 | (2006.01) |
| C07D 231/38 | (2006.01) |
| A61K 45/06 | (2006.01) |

(52) U.S. Cl.
CPC .......... *A61K 9/1635* (2013.01); *A61K 9/1694* (2013.01); *A61K 9/2009* (2013.01); *A61K 9/2013* (2013.01); *A61K 9/2027* (2013.01); *A61K 9/2054* (2013.01); *A61K 9/2086* (2013.01); *A61K 9/2095* (2013.01); *A61K 9/284* (2013.01); *A61K 9/2813* (2013.01); *A61K 9/2866* (2013.01); *A61K 31/155* (2013.01); *A61K 31/40* (2013.01); *A61K 31/403* (2013.01); *A61K 31/4035* (2013.01); *A61K 31/4439* (2013.01); *A61K 31/4985* (2013.01); *A61K 31/522* (2013.01); *A61K 31/7034* (2013.01); *A61K 45/06* (2013.01); *A61K 47/38* (2013.01); *A61P 3/10* (2018.01); *C07D 231/38* (2013.01); *C07D 403/12* (2013.01)

(58) Field of Classification Search
CPC .. A61K 9/2009; A61K 9/2013; A61K 9/2027; A61K 9/2054; A61K 9/2086; A61K 9/2095; A61K 9/2813; A61K 9/284; A61K 9/2866; A61K 31/155; A61K 31/40; A61K 31/403; A61K 31/4035; A61K 31/4439; A61K 31/4985; A61K 31/522; A61K 31/7034; A61K 45/06; A61K 47/38; A61K 31/70; A61K 31/7042; A61K 31/7048; A61K 9/28; A61K 31/7036; A61K 31/133; A61K 9/14; A61K 9/20; A61K 9/48; A61K 31/17; A61K 31/351; A61K 31/381; A61K 31/382; A61K 31/415; A61K 31/426; A61K 31/427; A61K 31/437; A61K 31/444; A61K 31/445; A61K 31/451; A61K 31/4965; A61K 31/497; A61K 31/506; A61K 31/64; A61K 31/7008; A61K 31/702; A61K 9/1652; A61K 9/2077; A61K 2300/00; A61K 31/49; A61K 31/00; A61K 31/47; A61K 31/496; A61P 3/10; A61P 1/16; A61P 3/00; A61P 3/04; A61P 3/08; A61P 5/50; A61P 9/12; A61P 25/28; A61P 9/10; A61P 13/12; A61P 1/04; A61P 11/06; A61P 13/02; A61P 15/00; A61P 9/00; A61P 25/00; C07D 231/38; C07D 403/12; C07D 215/20; C07D 209/18; C07D 211/52; C07D 211/64; C07D 273/00; C07D 277/68; C07D 295/215; C07D 215/54; G01N 2333/655; G01N 2500/04; G01N 2800/042; G01N 33/74; G01N 33/6893
See application file for complete search history.

(56) References Cited

U.S. PATENT DOCUMENTS

| | | | |
|---|---|---|---|
| 2009/0264445 A1* | 10/2009 | Berthel | ............ A61P 3/10 544/405 |
| 2014/0212487 A1* | 7/2014 | Mogalian | ............ A61K 9/1635 514/394 |
| 2016/0289208 A1 | 10/2016 | Kuroda et al. | |
| 2019/0328713 A1 | 10/2019 | Chen et al. | |

FOREIGN PATENT DOCUMENTS

| | | |
|---|---|---|
| EP | 1734040 A1 | 12/2006 |
| RU | 2544530 C2 | 3/2015 |
| WO | WO 2010/064735 A1 | 6/2010 |
| WO | WO 2011/149945 A1 | 12/2011 |
| WO | WO 2013/173417 A2 | 11/2013 |
| WO | WO-2013173417 A2 * | 11/2013 .......... A61K 31/426 |

OTHER PUBLICATIONS

Zhu et al., "Dorzagliatin (HMS5552), a novel dual-acting glucokinase activator, improves glycaemic control and pancreatic [beta]-cell function in patients with type 2 diabetes: A 28-day treatment study using biomarker-guided patient selection," *Diabetes, Obesity and Metabolism*, (20)9: 2113-2120 (2018).

Grewal et al., "Recent Updates on Glucokinase Activators for the Treatment of Type 2 Diabetes Mellitus," *Reviews in Medicinal Chemistry*, 14(7): 585-602 (2014).

Scheen, Andre J, "Investigational insulin secretagogues for type 2 diabetes," *Expert Opinion on Investigational Drugs*, 25(4): 405-422 (2016).

Rubaiy, Hussein N., "The therapeutic agents that target ATP-sensitive potassium channels," *Acta Pharm.*, 66: 23-34 (2016).

Zhai et al., "Pharmacokinetic and pharmacodynamics drug interaction study of piragliatin, a lucokinase activator, and glyburide, a sulfonylurea, in type 2 diabetic patients," *Clinical Pharmacol Drug Dev.*, 5(6):552-556 (2016).

Wang et al., "Recent Progress in Application of Therapeutic Drugs for Type 2 Diabetes Mellitus," *Progress in Pharmaceutical Sciences*, 41(6):434-443 (2017).

Yu, Gang, "Research Progress in Glucokinase Activators," *Progress in Pharmaceutical Sciences*, (40)3:168-177 (2016).

* cited by examiner

PHARMACEUTICAL COMBINATION, COMPOSITION AND COMPOUND PREPARATION CONTAINING GLUCOKINASE ACTIVATOR AND K-ATP CHANNEL BLOCKER, PREPARATION METHOD THEREFOR AND USE THEREOF

PRIORITY APPLICATION

This application is a national phase entry pursuant to 35 U.S.C. § 371 of International Application No. PCT/CN2019/088862, filed on May 28, 2019, which claims the priority of the Chinese patent application No. 201810556685.6, filed on May 31, 2018, the entire disclosure of each of which is incorporated herein by reference.

TECHNICAL FIELD

The present disclosure relates to a pharmaceutical combination, a composition and a fixed dose combination (FDC) formulation comprising a glucokinase activator (GKA) drug and a partner drug, to a preparation method thereof and to a use thereof in the treatment of some diseases.

More specifically, the present disclosure relates to a pharmaceutical combination, a pharmaceutical composition, or an oral solid formulation of a fixed dose combination comprising a glucokinase activator drug and a partner drug, and a preparation method thereof. The present disclosure also relates to the use of a pharmaceutical combination, a pharmaceutical composition or a fixed dose combination formulation comprising a glucokinase activator for the treatment and/or prevention of one or more diseases and medical disorders, including but not limited to type I diabetes, type II diabetes, maturity-onset diabetes of the young (MODY), diseases associated with islet dysfunction, impaired glucose tolerance, impaired fasting blood glucose, obesity and hypertension. In addition, the present disclosure also relates to a method for treating and/or preventing one or more diseases and medical disorders, comprising administering a therapeutically effective amount of the pharmaceutical combination, pharmaceutical composition or fixed dose combination formulation disclosed herein to a subject in need thereof.

BACKGROUND

Diabetes mellitus has become a prevalent disease worldwide, with 425 million patients over the world, and 120 million patients in China (International Diabetes Federation, Diabetes Atlas, 2015). Type II diabetes, i.e., non-insulin dependent diabetes mellitus (NIDDM), accounts for more than 90% of the patients with diabetes. Type II diabetes is a hyperglycemic, chronic, metabolic dysfunction resulting from an imbalance of blood glucose homeostasis in human body caused by insulin secretion disorder and insulin resistance. The blood glucose balance of the human body is mainly coordinated by two hormones that control blood glucose, including insulin and glucagon.

Glucose sensor glucokinase (GK) senses blood glucose changes, regulates the secretion of the messenger glucose-controlling hormones, insulin and glucagon, and GLP-1 (glucagon-like peptide-1), and constitutes a sensing system for steady-state regulation of human blood glucose. Glucose-controlling hormones control glucose storage during glucose uptake and glucose supply during fasting, constituting the steady-state regulation of human blood glucose. Organs involved in glucose storage are mainly liver, muscle and fat. Under the action of blood glucose and insulin, glucose is taken up and converted into liver glycogen, muscle glycogen and triglycerides. The main organ involved in glucose supply is liver. Under the action of blood glucose and glucagon, liver supplies glucose to a human body through liver glucose synthesis and liver glucose output. Insulin can also effectively regulate the activity of sodium-glucose cotransporter SGLT-2. When blood glucose rises, the glucose excreted by kidneys is reabsorbed for body's glucose storage. Glucose uptake and liver glucose output, as well as the use of glucose by various organs, constitute an operating system for a steady-state balance of the human blood glucose. The coordinated operation of the sensing system and the operating system of glucose constitute a random regulation of a steady-state of the human blood glucose.

In diabetic patients, the impaired function and expression of glucokinase, and the dysfunction of the sensor, result in the dysfunction of the early phase secretion of glucose-controlling hormones, affecting glucose uptake and output, and resulting in post-prandial hyperglycemia and pre-prandial hypoglycemia. Abnormal signaling of glucose-controlling hormones cause abnormal functions and expressions of key proteins in the execution system of glucose uptake and output, forming abnormal operating state, leading to type II diabetes.

Existing oral hypoglycemic drugs for diabetes usually act on a single glucose-controlling organ and cannot effectively treat the problem of imbalanced blood glucose homeostasis. Glucokinase activators represent a class of new drugs developed to treat or improve the disease state of patients with type II diabetes. For example, ((S)-2-[4-((2-chloro-phenoxy)-2-oxo-2,5-dihydro-pyrrol-1-yl]-4-methyl-pentanoic acid [1-((R)-2,3-dihydroxy-propyl)-1H-pyrazol-3-yl]-amide (referred to as HMS5552 hereinafter) can effectively improve the function of the glucose sensor in diabetic patients, and is currently the most promising drug for the treatment of diabetes to solve the above clinical needs.

SUMMARY

Diabetic patients often encounter such a situation during treatment that K-ATP channel blockers alone are not effective, and blood glucose cannot be controlled to an ideal level, especially after a period of use. In this regard, the inventors found that the combination of a K-ATP channel blocker and a glucokinase activator can significantly improve the hypoglycemic effect of the K-ATP channel blocker and reduce the safety risk, thus the pharmaceutical combination, composition and combination formulation comprising a glucokinase activator and a K-ATP channel blocker disclosed herein were obtained.

More specifically, the combination of a K-ATP channel blocker and a glucokinase activator can improve the function of multiple organs of patients in middle and late stages, and diabetes and accompanying diseases and complications were well treated. The number of pills taken by patients was reduced and the compliance of patients was improved, the total dose of drugs that achieve the same therapeutic effect was reduced, and the maximum efficacy was achieved with the lowest dose. It has a good effect and practical significance for the treatment or prevention of one or more of type I diabetes, type II diabetes, hyperglycemia, impaired glucose tolerance, obesity and other symptoms.

On the other hand, the fixed dose combination formulation comprising a glucokinase activator and a partner drug (the second or more active pharmaceutical ingredients)

disclosed herein not only has better therapeutic effects than the single use of each of these two or more drugs, but also solves the technical challenges that usually exist in combination formulations. The fixed dose combination formulation disclosed herein can provide the simultaneous release of two or more active ingredients with uniform content, and can optimize the dissolution rate of active ingredients contained in the formulation, especially making the active ingredients contained in the formulation quickly released in the pH environment of a small intestine. This is beneficial to the timely or simultaneous arrival of drugs in gut, pancreatic islet and liver target organs, achieving clinical advantages of multi-organs targeting, and synergistic hypoglycemic effect, and exhibiting a better therapeutic effect and reduced toxic or side effects. In addition, the fixed dose combination formulation comprising a glucokinase activator and a partner drug (the second or more active pharmaceutical ingredients) disclosed herein also has a short disintegration time, and good dissolution characteristics, and/or gives high bioavailability of the glucokinase activator in patients.

The present disclosure provides a pharmaceutical combination, a pharmaceutical composition, and a fixed dose combination formulation comprising a glucokinase activator, such as HMS5552 with the following structure, or an isotope labeled analogue thereof, or a pharmaceutically acceptable salt thereof, and other oral hypoglycemic drug, especially a solid formulation, such as an oral solid formulation such as a tablet,

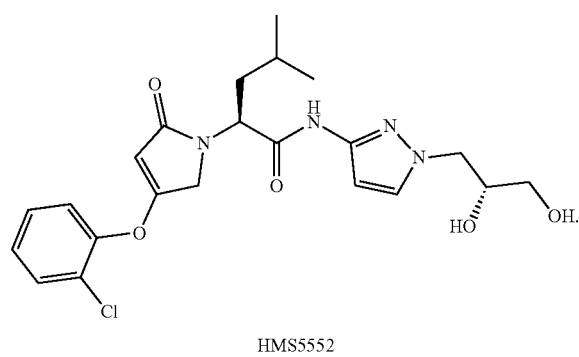 [SMILES: CC(C)C[C@@H](C(=O)Nc1ccn(C[C@@H](O)CO)n1)N1CC(Oc2ccccc2Cl)=CC1=O]

HMS5552

Specifically, the present disclosure also provides a pharmaceutical combination, a pharmaceutical composition, or a fixed dose combination formulation comprising a glucokinase activator drug such as HMS5552 or a pharmaceutically acceptable salt thereof and a K-ATP channel blocker including sulfonylurea secretagogues and non-sulfonylurea insulin secretagogues. Among them, preferably, examples of the sulfonylurea secretagogues include, but are not limited to, glibenclamide, glipizide, gliclazide, gliquidone and glimepiride, and a pharmaceutically acceptable salt thereof; and examples of the non-sulfonylurea insulin secretagogues include repaglinide and nateglinide, and a pharmaceutically acceptable salt thereof.

More specifically, the present disclosure also provides a fixed dose combination solid formulation comprising a glucokinase activator drug such as HMS5552 or a pharmaceutically acceptable salt thereof and a partner drug such as glimepiride. The solid formulation is preferably a tablet, or more preferably a coated tablet. In one embodiment, the glucokinase activator HMS5552 is in the form of a solid dispersion containing a polymer carrier.

More specifically, the present disclosure also provides a fixed dose combination solid formulation comprising a glucokinase activator drug such as HMS5552 or a pharmaceutically acceptable salt thereof and a partner drug such as repaglinide. The solid formulation is preferably a tablet, or more preferably a coated tablet. In one embodiment, the glucokinase activator HMS5552 is in the form of a solid dispersion containing a polymer carrier.

The present disclosure also provides a pharmaceutical combination, a pharmaceutical composition or a fixed dose combination formulation of a glucokinase activator drug and a partner drug (the second or more active pharmaceutical ingredients) prepared by a dry or wet processing method. The release mode of the pharmaceutical combination, pharmaceutical composition or fixed dose combination formulation disclosed herein is rapid release of the two or more active pharmaceutical ingredients.

The present disclosure also provides a pharmaceutical formulation comprising a glucokinase activator drug and a partner drug (the second or more active pharmaceutical ingredients), which has a short disintegration time and good dissolution characteristics and/or gives high bioavailability of the glucokinase activator in patients. The present disclosure also provides a method of preparing a pharmaceutical composition or a pharmaceutical formulation of a fixed dose combination of a glucokinase activator drug and a partner drug (the second or more active pharmaceutical ingredients, such as glimepiride or repaglinide) by a dry or wet processing method. The dry processing method includes dry compression (tableting) and dry granulation; and the wet processing method includes wet granulation.

The present disclosure also provides a pharmaceutical combination, a pharmaceutical composition or a pharmaceutical formulation comprising a glucokinase activator drug and a partner drug (the second or more active pharmaceutical ingredients), and a method for preventing, slowing down, delaying or treating a metabolic disorder (especially type II diabetes).

The present disclosure also provides a pharmaceutical combination, a pharmaceutical composition or a pharmaceutical formulation comprising a glucokinase activator drug and a partner drug (the second or more active pharmaceutical ingredients), and a method for improving blood glucose control in patients in need thereof, especially patients with type II diabetes.

The present disclosure also provides a pharmaceutical combination, a pharmaceutical composition or a pharmaceutical formulation comprising a glucokinase activator drug and a partner drug, and a method for improving blood glucose control in patients with insufficient blood glucose control.

The present disclosure also provides a pharmaceutical combination, a pharmaceutical composition or a pharmaceutical formulation comprising a glucokinase activator drug and a partner drug, and a method for preventing, slowing down or delaying maturity-onset diabetes of the young (MODY), diseases associated with islet dysfunction, impaired glucose tolerance (IGT), impaired fasting blood glucose (IFG), hypertension, insulin resistance and/or progression of metabolic syndrome to type II diabetes.

The present disclosure also provides a pharmaceutical combination, a pharmaceutical composition and a pharmaceutical formulation comprising a glucokinase activator drug and a partner drug, and a method for preventing, slowing down, delaying or treating a disease or a disorder including diabetes complications.

Other objects of the present disclosure will be apparent to those skilled in the art from the description and examples.

BRIEF DESCRIPTION OF THE EMBODIMENTS

The first aspect of the present disclosure provides a pharmaceutical combination, a pharmaceutical composition or a pharmaceutical formulation comprising the following components, a preparation method thereof, and a use thereof for treating diabetes and related diseases:
(a) a glucokinase activator, which is a compound selected from the following formula, or a pharmaceutically acceptable salt, an isotope labeled analogue, a crystalline form, a hydrate, a solvate, a diastereomeric or enantiomeric form thereof; preferably, the glucokinase activator is HMS5552; or more preferably, HMS5552 is present in the form of a solid dispersion,

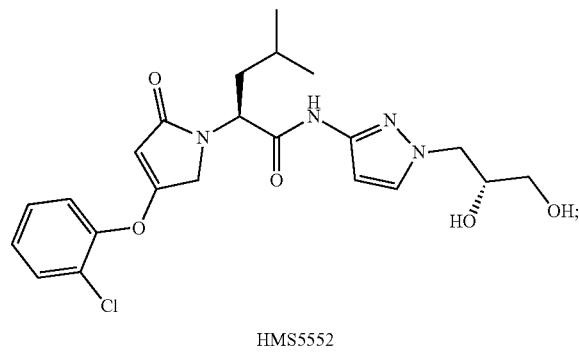 [SMILES: CC(C)C[C@@H](C(=O)Nc1ccn(C[C@@H](O)CO)n1)N1CC(Oc2ccccc2Cl)=CC1=O]

HMS5552

(b) a K-ATP channel blocker; and
(c) one or more excipients.

Another aspect of the present disclosure provides a pharmaceutical combination, a pharmaceutical composition or a pharmaceutical formulation comprising the following components, a preparation method thereof, and a use thereof for the treatment of diabetes and related diseases:
(a) a glucokinase activator, which is HMS5552 compound, or a pharmaceutically acceptable salt, an isotope labeled analogue, a crystalline form, a hydrate, a solvate, a diastereomeric or enantiomeric form thereof; preferably, the glucokinase activator is HMS5552; more preferably, HMS5552 is present in the form of a solid dispersion;
(b) glimepiride, repaglinide, or a pharmaceutically acceptable salt, an isotope labeled analogue, a crystalline form, a hydrate, a solvate, a diastereomeric or enantiomeric form thereof; and
(c) one or more excipients.

In particular, one aspect of the present disclosure also relates to a pharmaceutical combination, a pharmaceutical composition, and a pharmaceutical formulation comprising a fixed dose combination of a HMS5552 solid dispersion and a partner drug (e.g., glimepiride, repaglinide), and a preparation method thereof and a use thereof.

Definition

Unless otherwise specified, all technical and scientific terms used herein have the same meanings as commonly understood by those skilled in the art to which the present disclosure belongs, but in case of conflict, the definitions in this specification shall prevail.

As used in the specification and claims, the singular forms "a", "an" and "the (said)" include plural forms, unless the context clearly dictates otherwise.

Unless otherwise specified, the percentages (%) in the specification are all weight percentages (% by weight).

All numerical values or expressions related to component amounts, process conditions, etc. used in the specification and claims should be understood to be modified by "about" in all cases. The term "about" when referring to a quantity or a range of numerical values means that the quantity or the range of numerical values referred to is an approximate value within experimental variability (or within statistical experimental error). Therefore, the quantity or the range of numerical values can be varied between, for example, ±5 percent of the quantity or the range of numerical values.

All ranges involving the same components or properties include endpoints, which can be independently combined. Since these ranges are continuous, they include every value between the minimal and maximal values. It should also be understood that any numerical range cited in this application is intended to include all sub-ranges within that range.

When the present disclosure uses a range to define physical properties such as molecular weight or chemical properties, it shall include all combinations and sub-combinations of the range and specific embodiments therein. The term "comprising" (and related terms such as "containing" or "including" or "having") includes embodiments which are, for example, any combinations of substances, compositions, methods, or processes, etc., and are "consisted of the described features" or "essentially consisted of the described features".

As used in the specification and claims, "and/or" should be understood as "one or both" of the associated components, that is, the components coexist in some cases and exist separately in other cases. Multiple components listed with "and/or" should be understood in the same way, that is, "one or more" of the associated components. In addition to the components specifically identified in the "and/or" clause, other components may optionally be present, whether associated or not associated with those specifically identified components. Therefore, as a non-limiting example, when "A and/or B" is used to connect an open ending word such as "comprising", in one embodiment, it may only refer to A (optionally comprising components other than B); in another embodiment, it can only refer to B (optionally comprising components other than A); in yet another embodiment, it refers to A and B (optionally comprising other components), etc.

It should be understood that, unless explicitly indicated to the contrary, in any method that includes more than one step or one act claimed herein, the order of the steps and acts of the method is not necessarily limited to the order of the steps and acts of the method described.

The abbreviations used in the present disclosure have the common meanings in the fields of chemistry, biology and formulation.

Unless otherwise specified, the term "K-ATP channel blocker" or any substance thereof (e.g., "glimepiride", "repaglinide") in the context of the present disclosure is also intended to include any pharmaceutically acceptable salt, crystalline form, hydrate, solvate, diastereomer or enantiomer thereof.

HMS5552 (its former name is RO5305552, and English name is Dorzagliatin) has a chemical name of (S)-2-[4-(2-chloro-phenoxy)-2-oxo-2,5-dihydro-pyrrol-1-yl]-4-methyl-pentanoic acid [1-((R)-2,3-dihydroxy-propyl)-1H-pyrazol-3-yl]-amide.

Unless otherwise specified, % by weight (wt %) represents a percentage of the total weight of a pharmaceutical combination, a pharmaceutical composition or a pharmaceutical formulation.

A solid dispersion (SD) refers to a solid dispersion system formed by highly dispersing one or more active pharmaceutical ingredients into inactive adjuvants or carriers.

EUDRAGIT is the trade name of a synthetic pharmaceutical adjuvant. It includes copolymers of methacrylic acid and copolymers of methacrylate ester, collectively referred to as polyacrylic resins. Adjuvants based on polyacrylic resin are divided into different models according to their composition, proportion and degree of polymerization. Among them, Eudragit E is a polymer of dimethylaminoethyl methacrylate and methacrylate; Eudragit L is a polymer of methacrylic acid and methyl methacrylate with free carboxyl:ester of 1:1; and Eudragit S is a polymer of methacrylic acid and methyl methacrylate with free carboxyl:ester of 1:2.

The term "tablet" as used herein is intended to include compressed pharmaceutical formulations of all shapes and sizes, whether coated or not.

The terms "effective amount" or "therapeutically effective amount" refer to an amount of the agent sufficient to provide the desired biological result. The biological result may be a reduction and/or alleviation of the signs, symptoms, or causes of a disease, or any other desired alteration of a biological system. For example, an "effective amount" for therapeutic use is the necessary amount of the composition comprising a compound as the active ingredient as disclosed herein for providing a clinically significant decrease in a disease. An appropriate "effective" amount in any individual embodiment may be determined by one of ordinary skill in the art using routine experimentation. Thus, the expression "effective amount" generally refers to the quantity for which the active substance has therapeutic effects.

As used herein, the terms "treat" or "treatment" are synonymous with the term "prevent" and are meant to indicate a postponement of development of diseases, preventing the development of diseases, and/or reducing severity of such symptoms that will or are expected to develop. Thus, these terms include ameliorating existing disease symptoms, preventing additional symptoms, ameliorating or preventing the underlying metabolic causes of symptoms, inhibiting the disorder or disease, e.g., preventing the development of the disorder or disease, relieving the disorder or disease, causing a regression of the disorder or disease, relieving a condition caused by the disease or disorder, or stopping the symptoms of the disease or disorder.

By "pharmaceutically acceptable" or "pharmacologically acceptable", it is meant a material which is not biologically or otherwise undesirable, i.e., the material may be administered to an individual without causing a minimum of undesirable biological effects or interacting in a deleterious manner with any other components of the composition in which it is contained.

As used herein, the term "subject" encompasses mammals and non-mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the present disclosure, the mammal is a human.

A compound as an active ingredient in a pharmaceutical combination, a pharmaceutical composition or a pharmaceutical formulation (e.g., a fixed dose combination formulation) comprising a glucokinase activator disclosed herein may form a salt. Reference to a compound disclosed herein is understood to include reference to salts thereof, unless otherwise indicated. The term "salt(s)", as used herein, denotes acidic salts formed with inorganic and/or organic acids, as well as basic salts formed with inorganic and/or organic bases. In addition, when a compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compound may be formed, for example, by reacting the compound with an amount, such as an equivalent amount, of acid or base in a medium such as a medium from which the salt precipitates or in an aqueous medium (lyophilization after reaction).

Various compounds and salts, solvates, esters and prodrugs thereof, and polymorphs thereof are intended to be included in the disclosure.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are described below.

DETAILED DESCRIPTION OF THE EMBODIMENTS

Figure 1:
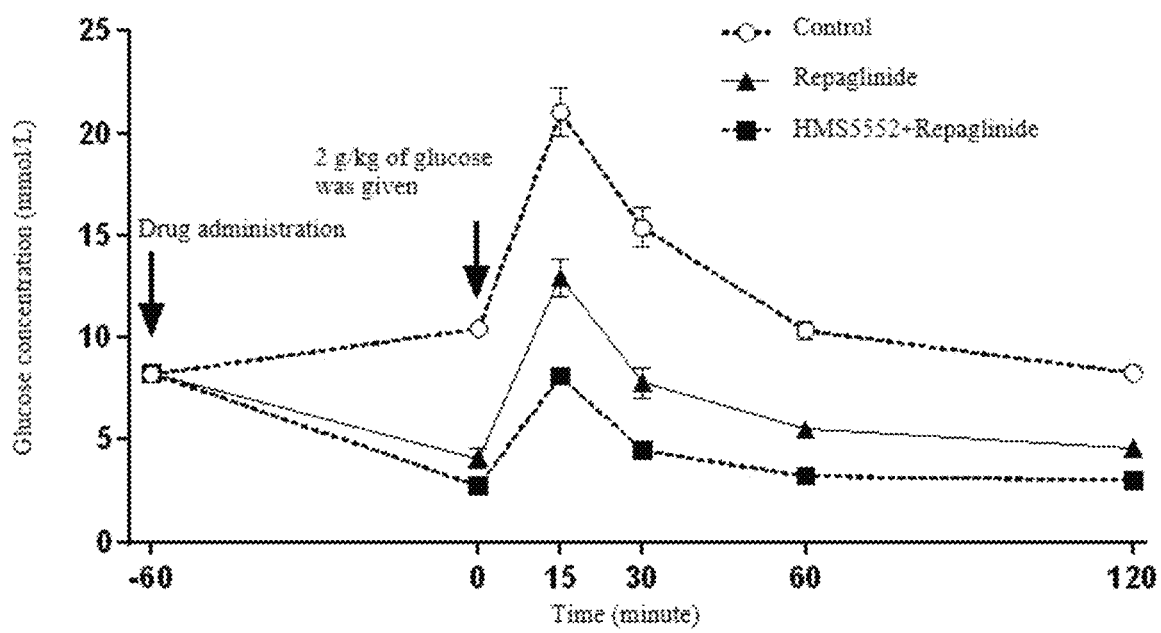
FIG. 1 shows the effect on blood glucose after glucose challenge in normal mice ($\overline{X}\pm s$, n=10) with the administration of repaglinide alone and the combination of HMS5552 and repaglinide.
Figure 2:
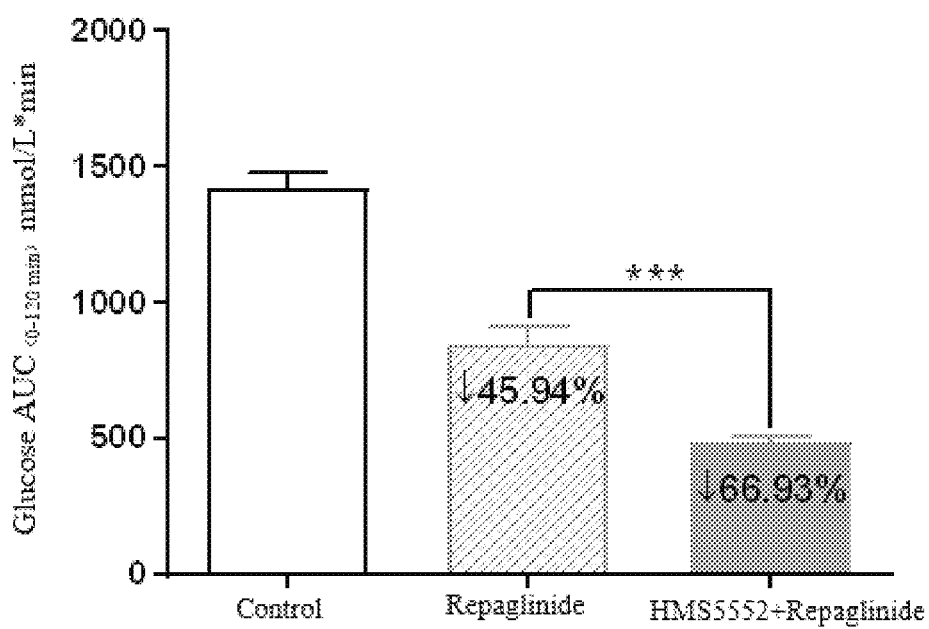
FIG. 2 shows the effect on $AUC_{0-120}$ min after glucose challenge in normal mice ($\overline{X}\pm s$, n=10; ***, P<0.001) with the administration of repaglinide alone and the combination of HMS5552 and repaglinide.

One aspect of the present disclosure relates to a pharmaceutical combination, a pharmaceutical composition or a pharmaceutical formulation such as a fixed dose combination formulation of a glucokinase activator (preferably, HMS5552 or an isotope labeled analogue or a pharmaceutically acceptable salt thereof) and a partner drug (e.g., glimepiride, repaglinide). The formulation can be powder, granule, tablet, capsule, sachet or other solid forms. Specifically, one aspect of the present disclosure relates to a tablet comprising a fixed dose combination of a glucokinase activator and a partner drug (e.g., glimepiride, repaglinide).

In a specific aspect of the present disclosure, the pharmaceutical combination, pharmaceutical composition or pharmaceutical formulation comprises:

(1) a glucokinase activator or a pharmaceutically acceptable salt thereof, or an isotope labeled analogue, a crystalline form, a hydrate, a solvate, a diastereomeric or enantiomeric form thereof; preferably, the glucokinase activator is HMS5552; more preferably, HMS5552 is present in the form of a solid dispersion, such as a solid dispersion (e.g., a spray-dried powder) comprising a polymer carrier;

(2) a K-ATP channel blocker; preferably selected from: glimepiride, repaglinide, or a pharmaceutically acceptable salt, an isotope labeled analogue, a crystalline form, a hydrate, a solvate, a diastereomeric or enantiomeric form thereof; and/or (3) filler(s); and/or (4) binder(s); and/or (5) disintegrant(s); and/or (6) lubricant(s) or glidant(s); and/or (7) coating agent(s).

In one embodiment disclosed herein, the pharmaceutical combination, pharmaceutical composition or pharmaceutical formulation may also contain one or more excipients selected from the group consisting of one or more binders; one or more diluents (fillers); one or more disintegrants; one or more lubricants; one or more glidants; one or more surfactants or wetting agents; one or more antioxidants; and one or more coating agents.

Pharmaceutical Combination, Pharmaceutical Composition, or Pharmaceutical Formulation Glucokinase Activator+K-ATP Channel Blocker In one embodiment, the present disclosure relates to a pharmaceutical combination, a pharmaceutical composition, or a pharmaceutical formulation (preferably, a fixed dose combination formulation), which comprises:

(a) a glucokinase activator, which is a compound represented by the following formulae, or a pharmaceutically acceptable salt, an isotope labeled analogue, a crystalline form, a hydrate, a solvate, a diastereomeric or enantiomeric form thereof,

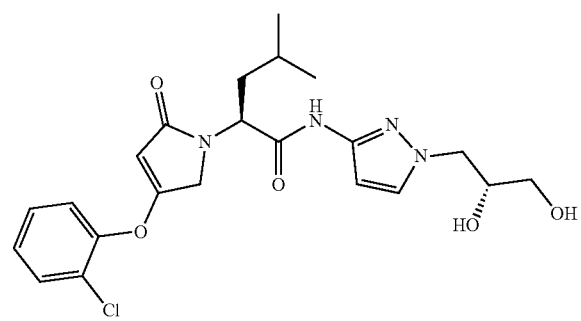

HMS5552

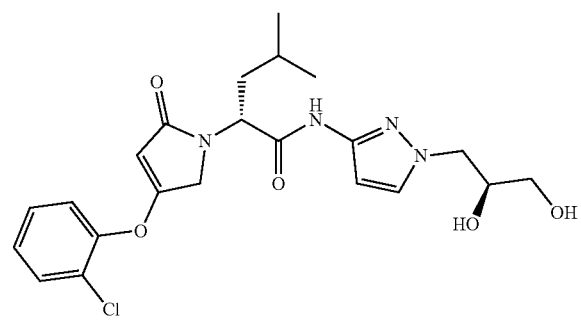

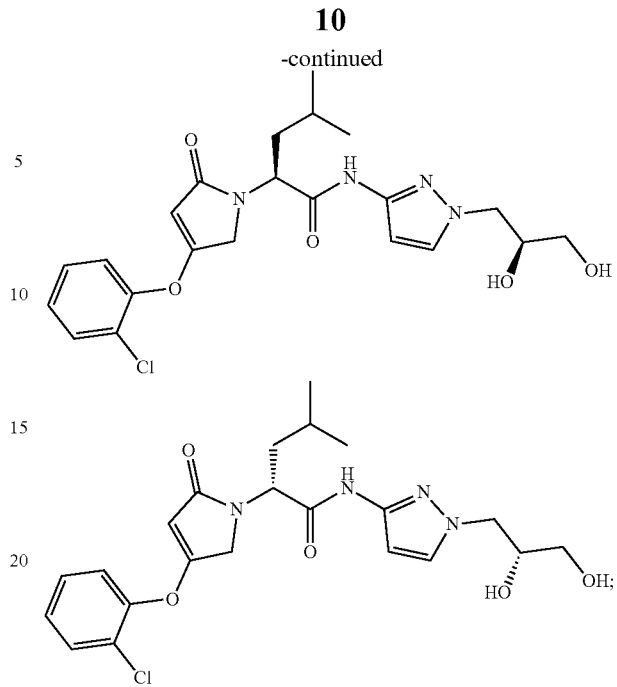

(b) a K-ATP channel blocker,
preferably, the K-ATP channel blocker includes sulfonylurea insulin secretagogues and non-sulfonylurea insulin secretagogues; wherein the sulfonylurea insulin secretagogues include glibenclamide, glipizide, gliclazide, gliquidone and glimepiride, and the non-sulfonylurea insulin secretagogues include repaglinide and nateglinide; preferably, glimepiride and repaglinide; and (c) one or more excipients;
wherein the above-mentioned drugs (a) and (b) are used simultaneously, separately or sequentially.

In one embodiment, in the above-mentioned pharmaceutical combination, pharmaceutical composition, or pharmaceutical formulation (preferably, a fixed dose combination formulation), the weight ratio of the glucokinase activator to the K-ATP channel blocker is about 400:1 to 10:1, preferably about 100:1 to 25:2, or more preferably about 25:2, about 25:1, about 50:1, about 75:2, about 75:1, or about 100:1.

In one embodiment, in the above-mentioned pharmaceutical combination, pharmaceutical composition, or pharmaceutical formulation (preferably, a fixed dose combination formulation), the glucokinase activator is present in a dose (preferably, a unit dose) ranging from about 1 mg to about 200 mg, or preferably about 25 mg to about 100 mg, preferably, wherein the dose (preferably, a unit dose) of the glucokinase activator is about 25 mg, about 50 mg, about 75 mg or about 100 mg.

In one embodiment, in the above-mentioned pharmaceutical combination, pharmaceutical composition, or pharmaceutical formulation, the K-ATP channel blocker is present in a dose (preferably, a unit dose) ranging from about 0.1 mg to about 10 mg, or preferably about 1 mg to about 5 mg, preferably, wherein the dose (preferably, a unit dose) of the K-ATP channel blocker is about 0.1 mg, about 0.2 mg, about 0.5 mg, about 1 mg, about 1.5 mg, about 2 mg, about 4 mg or about 5 mg, or still preferably about 1 mg or about 2 mg; and preferably, the K-ATP channel blocker is glimepiride or repaglinide.

In one embodiment, in the above-mentioned pharmaceutical combination, pharmaceutical composition, or pharmaceutical formulation (preferably, a fixed dose combination formulation), the above-mentioned glucokinase activator is the compound HMS5552, or an isotope labeled analogue, or a pharmaceutically acceptable salt thereof,

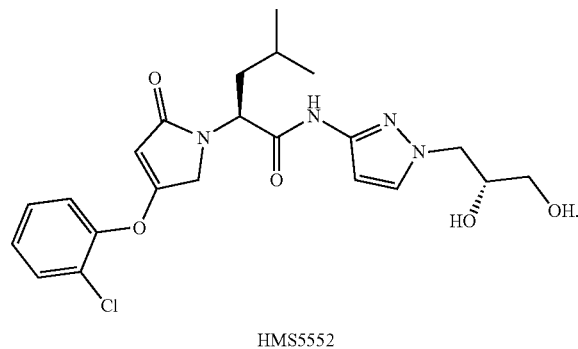 [SMILES: CC(C)C[C@@H](C(=O)Nc1ccn(C[C@@H](O)CO)n1)N1CC(Oc2ccccc2Cl)=CC1=O]

HMS5552

In one embodiment, in the above-mentioned pharmaceutical combination, pharmaceutical composition, or pharmaceutical formulation (preferably, a fixed dose combination formulation), the glucokinase activator is present in the form of a solid dispersion.

In one embodiment, the solid dispersion is obtained by spray drying, hot melting or freeze drying of a glucokinase activator, or an isotope labeled analogue, or a pharmaceutically acceptable salt thereof, together with a polymer carrier.

In one embodiment, the amount of the glucokinase activator in the solid dispersion, based on the total weight of the solid dispersion, may vary from about 1% to about 99% by weight, or preferably from 10% to 90% by weight. In one embodiment, the amount of the glucokinase activator is about 1% by weight, about 2% by weight, about 3% by weight, about 4% by weight, about 5% by weight, about 6% by weight, about 7% by weight, about 8% by weight, about 9% by weight, about 10% by weight, about 11% by weight, about 12% by weight, about 13% by weight, about 14% by weight, about 15% by weight, about 16% by weight, about 17% by weight, about 18% by weight, about 19% by weight, about 20% by weight, about 21% by weight, about 22% by weight, about 23% by weight, about 24% by weight, about 25% by weight, about 26% by weight, about 27% by weight, about 28% by weight, about 29% by weight, about 30% by weight, about 31% by weight, about 32% by weight, about 33% by weight, about 34% by weight, about 35% by weight, about 36% by weight, about 37% by weight, about 38% by weight, about 39% by weight, about 40% by weight, about 41% by weight, about 42% by weight, about 43% by weight, about 44% by weight, about 45% by weight, about 46% by weight, about 47% by weight, about 48% by weight, about 49% by weight, about 50% by weight, about 51% by weight, about 52% by weight, about 53% by weight, about 54% by weight, about 55% by weight, about 56% by weight, about 57% by weight, about 58% by weight, about 59% by weight, about 60% by weight, about 61% by weight, about 62% by weight, about 63% by weight, about 64% by weight, about 65% by weight, about 66% by weight, about 67% by weight, about 68% by weight, about 69% by weight, about 70% by weight, about 71% by weight, about 72% by weight, about 73% by weight, about 74% by weight, about 75% by weight, about 76% by weight, about 77% by weight, about 78% by weight, about 79% by weight, about 80% by weight, about 81% by weight, about 82% by weight, about 83% by weight, about 84% by weight, about 85% by weight, about 86% by weight, about 87% by weight, about 88% by weight, about 89% by weight, about 90% by weight, about 91% by weight, about 92% by weight, about 93% by weight, about 94% by weight, about 95% by weight, about 96% by weight, about 97% by weight, about 98% by weight, or about 99% by weight, or any range therebetween.

In one embodiment, the amount of the glucokinase activator in the solid dispersion, based on the total weight of the solid dispersion, is about 1% to about 20% by weight, about 2% to about 40% by weight, about 30% to about 60% by weight, about 60% to about 80% by weight, about 70% to about 90% by weight, or about 80% to about 100% by weight.

In one embodiment, in the above-mentioned pharmaceutical combination, pharmaceutical composition or pharmaceutical formulation (preferably, a fixed dose combination formulation), the glucokinase activator is the compound HMS5552, an isotope labeled analogue thereof or a pharmaceutically acceptable salt thereof, which is combined with a polymer carrier to obtain a solid dispersion by spray drying, hot melting or freeze drying, etc.

In one embodiment, in the above-mentioned pharmaceutical combination, pharmaceutical composition or pharmaceutical formulation (preferably, a fixed dose combination formulation), the polymer carrier in the solid dispersion is selected from a polypropylene resin-based polymer, which is a polymeric compound derived from the polymerization of acrylic acid (or methacrylic acid and esters thereof such as methyl ester, ethyl esters and the like) (as monomer), or derived from the polymerization of two monomers (binary polymerization) or three monomers (ternary polymerization) in a certain ratio using acrylic acid and methacrylic acid (or its ester such as methyl ester, ethyl ester, dimethylaminoethyl ester, etc.).

In one embodiment, in the above-mentioned pharmaceutical combination, pharmaceutical composition, or pharmaceutical formulation (preferably, a fixed dose combination formulation), the glucokinase activator is present in the form of a solid dispersion, and the weight ratio of the solid dispersion of the glucokinase activator to the K-ATP channel blocker is about 400:1 to 20:1, preferably about 200:1 to 25:1, or more preferably about 25:1, about 50:1, about 100:1, about 75:1, about 150:1 or about 200:1.

In one embodiment, the polymer carrier used in the solid dispersion in the above-mentioned pharmaceutical combination, pharmaceutical composition or pharmaceutical formulation (preferably, a fixed dose combination formulation) is selected from the group consisting of copolymer of butyl methacrylate, dimethylaminoethyl methacrylate and methyl methacrylate; copolymer of methacrylic acid and ethyl acrylate; copolymer of methacrylic acid and methyl methacrylate; copolymer of ethyl acrylate, methyl methacrylate and chlorotrimethylamino ethyl methacrylate; copolymer of ethyl acrylate and methyl methacrylate; copolymer of methacrylic acid, methyl acrylate and methyl methacrylate, and copolymer of methacrylic acid and butyl acrylate.

In one embodiment, the above-mentioned polymer carrier is selected from the group consisting of copolymer of butyl methacrylate, dimethylaminoethyl methacrylate and methyl methacrylate (1:2:1), copolymer of methacrylic acid and ethyl acrylate (1:1), copolymer of methacrylic acid and methyl methacrylate (1:2), copolymer of ethyl acrylate, methyl methacrylate and chlorotrimethylamino ethyl methacrylate (1:2:0.2), copolymer of ethyl acrylate, methyl methacrylate and chlorotrimethylamino ethyl methacrylate (1:2:0.1), copolymer of ethyl acrylate and methyl methacrylate (2:1), copolymer of methacrylic acid and butyl acrylate (35:65), copolymer of methacrylic acid and methyl methacrylate (1:1), copolymer of methacrylic acid and methyl methacrylate (35:65).

In one embodiment, the above-mentioned polymer carrier is Eudragit, including Eudragit E, Eudragit L, Eudragit S, Eudragit RL and Eudragit RS, wherein Eudragit E is produced by the polymerization of dimethylamino methacrylate and other neutral methacryates, including copolymers of dimethylaminoethyl methacrylate and methacrylate; Eudragit L and Eudragit S is produced by the polymerization of methacrylic acid and methacrylates in various ratios, including a copolymer of methacrylic acid and methyl methacrylate with 1:1 of free carboxyl:ester or a copolymer of methacrylic acid and methyl methacrylate with 1:2 of free carboxyl:ester; Eudragit RL and Eudragit RS type is a copolymer of acrylic acid containing some quaternary amine groups and methacrylate, including the copolymer of acrylic acid containing 10% quaternary amine group and methacrylate and the copolymer of acrylic acid containing 5% quaternary amine group and methacrylate.

In one embodiment, the above-mentioned polymer carrier is selected from the group consisting of:
Eudragit E100, which is copolymer of butyl methacrylate, dimethylaminoethyl methacrylate and methyl methacrylate (1:2:1), including Eudragit E PO;
Eudragit L100, methacrylic acid copolymer of type A, which is an anionic copolymer of methacrylic acid and methyl methacrylate (1:1); and
Eudragit S100, which is copolymer of methacrylic acid and methyl methacrylate (1:2).

In one embodiment, in the above-mentioned pharmaceutical combination, pharmaceutical composition or pharmaceutical formulation (preferably, a fixed dose combination formulation), the polymer carrier in the solid dispersion of HMS5552 is methacrylic acid copolymer of type A (an anionic copolymer of methacrylic acid and methyl methacrylate (1:1)), preferably Eudragit, or more preferably Eudragit L100.

In one embodiment, in the above-mentioned pharmaceutical combination, pharmaceutical composition or pharmaceutical formulation (preferably, a fixed dose combination formulation), the weight ratio of HMS5552 to Eudragit L100 in the solid dispersion of HMS5552 is about 1:10 to 10:1, about 1:9 to 9:1, about 2:3 to 9:1, about 3:4 to 9:1, about 4:5 to 9:1, about 5:6 to 9:1, or about 1:1 to 9:1; preferably, about 2:3 to 4:1, about 3:4 to 4:1, about 4:5 to 4:1, about 5:6 to 4:1, or about 1:1 to 4:1; preferably, about 2:3 to 7:3, about 3:4 to 7:3, about 4:5 to 7:3, about 5:6 to 7:3, or about 1:1 to 7:3; preferably, about 2:3 to 3:2, about 3:4 to 4:3, about 4:5 to 5:4, or about 5:6 to 6:5; preferably, about 1:4 to 4:1, about 3:7 to 7:3, about 2:3 to 3:2, about 3:4 to 4:3, about 4:5 to 5:4, or about 5:6 to 6:5, or any range therebetween.

In one embodiment, in the above-mentioned pharmaceutical combination, pharmaceutical composition or pharmaceutical formulation (preferably, a fixed dose combination formulation), the weight ratio of HMS5552 to Eudragit L100 in the solid dispersion of HMS5552 is about 1:1, about 2:3, about 3:2, about 1:4, about 4:1, about 3:4, about 4:3, about 4:5, about 5:4, about 5:6, about 6:5, about 7:3, about 3:7, about 1:9, about 9:1, or any range therebetween.

In one embodiment, in the above-mentioned pharmaceutical combination, pharmaceutical composition, or pharmaceutical formulation (preferably, a fixed dose combination formulation), the second active ingredient is glimepiride. The above-mentioned pharmaceutical combination, pharmaceutical composition, or fixed dose combination formulation of the glucokinase activator (HMS5552 or an isotope labeled analogue or a pharmaceutically acceptable salt thereof) and glimepiride contains (by weight): about 1-99% of the glucokinase activator (preferably, HMS5552 or an isotope labeled analogue or a pharmaceutically acceptable salt thereof); about 0.1-15% of glimepiride; about 0-85% of filler(s); about 1-25% of binder(s); about 0-15% of disintegrant(s); about 0.1-10% of lubricant(s); about 0-3% of glidant(s); and about 0-5% of coating agent(s). The pharmaceutical composition or pharmaceutical formulation (preferably, a fixed dose combination formulation) is prepared by a wet granulation method or a dry granulation method, preferably by a wet granulation method.

In one embodiment, in the above-mentioned pharmaceutical combination, pharmaceutical composition, or pharmaceutical formulation (preferably, a fixed dose combination formulation) of the glucokinase activator (HMS5552 or an isotope labeled analogue or a pharmaceutically acceptable salt thereof) and glimepiride, the dose (preferably, a unit dose) of the glucokinase activator (preferably, HMS5552 or an isotope labeled analogue or a pharmaceutically acceptable salt thereof) is about 1 mg to 200 mg. The preferable dose (preferably, a unit dose) of the glucokinase activator is about 5 mg to 100 mg. Preferably, the dose (preferably, a unit dose) of the glucokinase activator is about 5 mg, about 10 mg, about 20 mg, about 25 mg, about 30 mg, about 40 mg, about 50 mg, about 60 mg, about 75 mg, about 80 mg, about 90 mg, about 100 mg, or any range therebetween. More preferably, the dose (preferably, a unit dose) of the glucokinase activator (preferably, HMS5552 or an isotope labeled analogue or a pharmaceutically acceptable salt thereof) is about 25 mg, about 50 mg, about 75 mg, or about 100 mg. Preferably, in the above-mentioned pharmaceutical combination, pharmaceutical composition, or pharmaceutical formulation (preferably, a fixed dose combination formulation), HMS5552 is present in the form of a solid dispersion.

In one embodiment, in the above-mentioned pharmaceutical combination, pharmaceutical composition, or pharmaceutical formulation (preferably, a fixed dose combination formulation) of the glucokinase activator (HMS5552 or an isotope labeled analogue or a pharmaceutically acceptable salt thereof) and glimepiride, the dose (preferably, a unit dose) of glimepiride is about 1 mg to about 4 mg. Preferably, the dose (preferably, a unit dose) of glimepiride is about 1 mg, about 2 mg, or about 4 mg. Preferably, in the above-mentioned pharmaceutical combination, pharmaceutical composition, or pharmaceutical formulation (preferably, a fixed dose combination formulation), HMS5552 is present in the form of a solid dispersion.

In the pharmaceutical combination, pharmaceutical composition, or fixed dose combination formulation of the present disclosure, the specific embodiments of the doses (preferably, unit doses) of HMS5552 (or an isotope labeled analogue or a pharmaceutically acceptable salt thereof) and glimepiride are as follows:
(1) about 25 mg of HMS5552 and about 1 mg of glimepiride;
(2) about 50 mg of HMS5552 and about 1 mg of glimepiride;
(3) about 75 mg of HMS5552 and about 1 mg of glimepiride;
(4) about 100 mg of HMS5552 and about 1 mg of glimepiride;
(5) about 25 mg of HMS5552 and about 2 mg of glimepiride;

(6) about 50 mg of HMS5552 and about 2 mg of glimepiride;
(7) about 75 mg of HMS5552 and about 2 mg of glimepiride; and
(8) about 100 mg of HMS5552 and about 2 mg of glimepiride;
preferably, in the above-mentioned pharmaceutical combination, pharmaceutical composition, or pharmaceutical formulation (preferably, a fixed dose combination formulation), HMS5552 is present in the form of a solid dispersion.

In one embodiment, the preferable dosage form of the pharmaceutical combination, pharmaceutical composition, or pharmaceutical formulation (preferably, a fixed dose combination formulation) of the present disclosure is a tablet.

In one embodiment, the above-mentioned tablet is a fixed dose combination tablet of the glucokinase activator (HMS5552 or an isotope labeled analogue or a pharmaceutically acceptable salt thereof) and glimepiride.

In one embodiment, the pharmaceutical combination, pharmaceutical composition, or pharmaceutical formulation (preferably, a fixed dose combination tablet, which is a tablet of 25 mg glucokinase activator (preferably, HMS5552 or an isotope labeled analogue or a pharmaceutically acceptable salt thereof)/1 mg glimepiride) comprises the components with the following amounts (by weight): about 25 mg of the glucokinase activator (preferably, HMS5552 or an isotope labeled analogue or a pharmaceutically acceptable salt thereof); about 1 mg of glimepiride; about 0-75% of optional filler(s); about 2-8% of binder(s); about 1-5% of disintegrant(s); about 0.5-3% of lubricant(s); about 0-0.5% of glidant(s) and about 0-5% of coating agent(s); preferably, the above-mentioned glucokinase activator is in the form of a solid dispersion as described above, or preferably the solid dispersion contains a glucokinase activator and a polymer carrier, or preferably contains about 1:1 of the glucokinase activator and Eudragit L100.

In one embodiment, the pharmaceutical combination, pharmaceutical composition, or pharmaceutical formulation (preferably, a fixed dose combination tablet, which is a tablet of 50 mg glucokinase activator (preferably, HMS5552 or an isotope labeled analogue or a pharmaceutically acceptable salt thereof)/1 mg glimepiride) contains the components with the following amounts (by weight): about 50 mg of the glucokinase activator (preferably, HMS5552 or an isotope labeled analogue or a pharmaceutically acceptable salt thereof); about 1 mg of glimepiride; about 0-75% of optional filler(s); about 2-8% of binder(s); about 1-5% of disintegrant(s); about 0.5-3% of lubricant(s); about 0-0.5% of glidant(s) and about 0-5% of coating agent(s); preferably, the above-mentioned glucokinase activator is in the form of a solid dispersion as described above, or preferably the solid dispersion contains a glucokinase activator and a polymer carrier, or preferably contains about 1:1 of the glucokinase activator and Eudragit L100.

In one embodiment, the pharmaceutical combination, pharmaceutical composition, or pharmaceutical formulation (preferably, a fixed dose combination tablet, which is a tablet of 75 mg glucokinase activator (preferably, HMS5552 or an isotope labeled analogue or a pharmaceutically acceptable salt thereof)/1 mg glimepiride) comprises the components with the following amounts (by weight): about 75 mg of the glucokinase activator (preferably, HMS5552 or an isotope labeled analogue or a pharmaceutically acceptable salt thereof); about 1 mg of glimepiride; about 0-75% of optional filler(s); about 2-8% of binder(s); about 1-5% of disintegrant(s); about 0.5-3% of lubricant(s); about 0-0.5% of glidant(s) and about 0-5% of coating agent(s); preferably, the above-mentioned glucokinase activator is in the form of a solid dispersion as described above, or preferably the solid dispersion contains a glucokinase activator and a polymer carrier, or preferably contains about 1:1 of the glucokinase activator and Eudragit L100.

In one embodiment, the pharmaceutical combination, pharmaceutical composition, or pharmaceutical formulation (preferably, a fixed dose combination tablet, which is a tablet of 100 mg glucokinase activator (preferably, HMS5552 or an isotope labeled analogue or a pharmaceutically acceptable salt thereof)/1 mg glimepiride) comprises the components with the following amounts (by weight): about 100 mg of the glucokinase activator (preferably, HMS5552 or an isotope labeled analogue or a pharmaceutically acceptable salt thereof); about 1 mg of glimepiride; about 0-75% of optional filler(s); about 2-8% of binder(s); about 1-5% of disintegrant(s); about 0.5-3% of lubricant(s); about 0-0.5% of glidant(s) and about 0-5% of coating agent(s); preferably, the above-mentioned glucokinase activator is in the form of a solid dispersion as described above, or preferably the solid dispersion contains a glucokinase activator and a polymer carrier, or preferably contains about 1:1 of the glucokinase activator and Eudragit L100.

In one embodiment, the pharmaceutical combination, pharmaceutical composition, or pharmaceutical formulation (preferably, a fixed dose combination tablet, which is a tablet of 25 mg glucokinase activator (preferably, HMS5552 or an isotope labeled analogue or a pharmaceutically acceptable salt thereof)/2 mg glimepiride) comprises the components with the following amounts (by weight): about 25 mg of the glucokinase activator (preferably, HMS5552 or an isotope labeled analogue or a pharmaceutically acceptable salt thereof); about 2 mg of glimepiride; about 0-75% of optional filler(s); about 2-8% of binder(s); about 1-5% of disintegrant(s); about 0.5-3% of lubricant(s); about 0-0.5% of glidant(s) and about 0-5% of coating agent(s); preferably, the above-mentioned glucokinase activator is in the form of a solid dispersion as described above, or preferably the solid dispersion contains a glucokinase activator and a polymer carrier, or preferably contains about 1:1 of the glucokinase activator and Eudragit L100.

In one embodiment, the pharmaceutical combination, pharmaceutical composition, or pharmaceutical formulation (preferably, a fixed dose combination tablet, which is a tablet of 50 mg glucokinase activator (preferably, HMS5552 or an isotope labeled analogue or a pharmaceutically acceptable salt thereof)/2 mg glimepiride) comprises the components with the following amounts (by weight): about 50 mg of the glucokinase activator (preferably, HMS5552 or an isotope labeled analogue or a pharmaceutically acceptable salt thereof); about 2 mg of glimepiride; about 0-75% of optional filler(s); about 2-8% of binder(s); about 1-5% of disintegrant(s); about 0.5-3% of lubricant(s); about 0-0.5% of glidant(s) and about 0-5% of coating agent(s); preferably, the above-mentioned glucokinase activator is in the form of a solid dispersion as described above, or preferably the solid dispersion contains a glucokinase activator and a polymer carrier, or preferably contains about 1:1 of the glucokinase activator and Eudragit L100.

In one embodiment, the pharmaceutical combination, pharmaceutical composition, or pharmaceutical formulation (preferably, a fixed dose combination tablet, which is a tablet of 75 mg glucokinase activator (preferably, HMS5552 or an isotope labeled analogue or a pharmaceutically acceptable salt thereof)/2 mg glimepiride) comprises the components with the following amounts (by weight): about 75 mg of the glucokinase activator (preferably, HMS5552 or an isotope labeled analogue or a pharmaceutically acceptable salt thereof); about 2 mg of glimepiride; about 0-75% of optional filler(s); about 2-8% of binder(s); about 1-5% of disintegrant(s); about 0.5-3% of lubricant(s); about 0-0.5% of glidant(s) and about 0-5% of coating agent(s); preferably, the above-mentioned glucokinase activator is in the form of a solid dispersion as described above, or preferably the solid dispersion contains a glucokinase activator and a polymer carrier, or preferably contains about 1:1 of the glucokinase activator and Eudragit L100.

In one embodiment, the pharmaceutical combination, pharmaceutical composition, or pharmaceutical formulation (preferably, a fixed dose combination tablet, which is a tablet of 100 mg glucokinase activator (preferably, HMS5552 or an isotope labeled analogue or a pharmaceutically acceptable salt thereof)/2 mg glimepiride) comprises the components with the following amounts (by weight): about 100 mg of the glucokinase activator (preferably, HMS5552 or an isotope labeled analogue or a pharmaceutically acceptable salt thereof); about 2 mg of glimepiride; about 0-75% of optional filler(s); about 2-8% of binder(s); about 1-5% of disintegrant(s); about 0.5-3% of lubricant(s); about 0-0.5% of glidant(s) and about 0-5% of coating agent(s); preferably, the above-mentioned glucokinase activator is in the form of a solid dispersion as described above, or preferably the solid dispersion contains a glucokinase activator and a polymer carrier, or preferably contains about 1:1 of the glucokinase activator and Eudragit L100.

In one embodiment, in the above-mentioned pharmaceutical combination, pharmaceutical composition, or pharmaceutical formulation (preferably, a fixed dose combination formulation), the second active ingredient is repaglinide. The above-mentioned pharmaceutical combination, pharmaceutical composition, or fixed dose combination formulation of the glucokinase activator (HMS5552 or an isotope labeled analogue or a pharmaceutically acceptable salt thereof) and repaglinide contains (by weight): about 1 to 99.5% of the glucokinase activator (preferably, HMS5552 or an isotope labeled analogue or a pharmaceutically acceptable salt thereof); about 0.05 to 8% of repaglinide; about 0 to 90% of filler(s); about 1 to 25% of binder(s); about 0-15% of disintegrant(s); about 0.1-10% of lubricant(s); about 0-3% of glidant(s); and about 0-5% of coating agent(s). The pharmaceutical composition or pharmaceutical formulation (preferably, a fixed dose combination formulation) is prepared by a wet granulation method or a dry granulation method, preferably by a wet granulation method.

In one embodiment, in the above-mentioned pharmaceutical combination, pharmaceutical composition, or pharmaceutical formulation (preferably, a fixed dose combination formulation) of the glucokinase activator (HMS5552 or an isotope labeled analogue or a pharmaceutically acceptable salt thereof) and repaglinide, the dose (preferably, a unit dose) of the glucokinase activator (preferably, HMS5552 or an isotope labeled analogue or a pharmaceutically acceptable salt thereof) is about 1 mg to 200 mg. The alternative dose (preferably, a unit dose) of the glucokinase activator is about 5 mg to 100 mg. Preferably, the dose (preferably, a unit dose) of the glucokinase activator is about 5 mg, about 10 mg, about 20 mg, about 25 mg, about 30 mg, about 40 mg, about 50 mg, about 60 mg, about 75 mg, about 80 mg, about 90 mg, about 100 mg, or any range therebetween. More preferably, the dose (preferably, a unit dose) of the glucokinase activator (preferably, HMS5552 or an isotope labeled analogue or a pharmaceutically acceptable salt thereof) is about 25 mg, about 50 mg, about 75 mg, or about 100 mg. Preferably, in the above-mentioned pharmaceutical combination, pharmaceutical composition, or pharmaceutical formulation (preferably, a fixed dose combination formulation), HMS5552 is present in the form of a solid dispersion.

In one embodiment, in the above-mentioned pharmaceutical combination, pharmaceutical composition, or pharmaceutical formulation (preferably, a fixed dose combination formulation) of the glucokinase activator (HMS5552 or an isotope labeled analogue or a pharmaceutically acceptable salt thereof) and repaglinide, the dose (preferably, a unit dose) of repaglinide is about 0.5 mg to about 2 mg. Preferably, the dose (preferably, a unit dose) of repaglinide is about 0.5 mg, about 1 mg or about 2 mg. Preferably, in the above-mentioned pharmaceutical combination, pharmaceutical composition, or pharmaceutical formulation (preferably, a fixed dose combination formulation), HMS5552 is present in the form of a solid dispersion.

In the pharmaceutical combination, pharmaceutical composition, or fixed dose combination formulation composition of the present disclosure, the specific embodiments of the doses (preferably, unit doses) of HMS5552 and repaglinide are as follows:
(1) about 25 mg of HMS5552 and about 1 mg of repaglinide;
(2) about 50 mg of HMS5552 and about 1 mg of repaglinide;
(3) about 75 mg of HMS5552 and about 1 mg of repaglinide;
(4) about 100 mg of HMS5552 and about 1 mg of repaglinide;
(5) about 25 mg of HMS5552 and about 2 mg of repaglinide;
(6) about 50 mg of HMS5552 and about 2 mg of repaglinide;
(7) about 75 mg of HMS5552 and about 2 mg of repaglinide; and
(8) about 100 mg of HMS5552 and about 2 mg of repaglinide.

Preferably, in the above-mentioned pharmaceutical combination, pharmaceutical composition, or pharmaceutical formulation (preferably, a fixed dose combination formulation), HMS5552 is present in the form of a solid dispersion.

In one embodiment, the preferable dosage form of the pharmaceutical combination, pharmaceutical composition, or pharmaceutical formulation (preferably, a fixed dose combination formulation) of the present disclosure is a tablet.

In one embodiment, the above-mentioned tablet is a fixed dose combination tablet of the glucokinase activator (HMS5552 or an isotope labeled analogue or a pharmaceutically acceptable salt thereof) and repaglinide.

In one embodiment, the pharmaceutical combination, pharmaceutical composition, or pharmaceutical formulation (preferably, a fixed dose combination tablet, which is a tablet of 25 mg glucokinase activator (preferably, HMS5552 or an isotope labeled analogue or a pharmaceutically acceptable salt thereof)/1 mg repaglinide) comprises the components with the following amounts (by weight): about 25 mg of the glucokinase activator, HMS5552 or an isotope labeled analogue or a pharmaceutically acceptable salt thereof); about 1 mg of repaglinide; about 0-90% of optional filler(s); about 1-25% of binder(s); about 1-15% of disintegrant(s); about 0.5-3% of lubricant(s); about 0-0.5% of glidant(s) and about 0-5% of coating agent(s); wherein the above-mentioned glucokinase activator is in the form of a solid dispersion as described above.

In one embodiment, the pharmaceutical combination, pharmaceutical composition, or pharmaceutical formulation (preferably, a fixed dose combination tablet, which is a tablet of 50 mg glucokinase activator (preferably, HMS5552 or an isotope labeled analogue or a pharmaceutically acceptable salt thereof)/1 mg repaglinide) comprises the components with the following amounts (by weight): about 50 mg of the glucokinase activator (preferably, HMS5552 or an isotope labeled analogue or a pharmaceutically acceptable salt thereof); about 1 mg of repaglinide; about 0-90% of optional filler(s); about 1-25% of binder(s); about 1-15% of disintegrant(s); about 0.5-3% of lubricant(s); about 0-0.5% of glidant(s) and about 0-5% of coating agent(s); wherein the above-mentioned glucokinase activator is in the form of a solid dispersion as described above.

In one embodiment, the pharmaceutical combination, pharmaceutical composition, or pharmaceutical formulation (preferably, a fixed dose combination tablet, which is a tablet of 75 mg glucokinase activator (preferably, HMS5552 or an isotope labeled analogue or a pharmaceutically acceptable salt thereof)/1 mg repaglinide) comprises the components with the following amounts (by weight): about 75 mg of the glucokinase activator (preferably, HMS5552 or an isotope labeled analogue or a pharmaceutically acceptable salt thereof); about 1 mg of repaglinide; about 0-90% of optional filler(s); about 1-25% of binder(s); about 1-15% of disintegrant(s); about 0.5-3% of lubricant(s); about 0-0.5% of glidant(s) and about 0-5% of coating agent(s); wherein the above-mentioned glucokinase activator is in the form of a solid dispersion as described above.

In one embodiment, the pharmaceutical combination, pharmaceutical composition, or pharmaceutical formulation (preferably, a fixed dose combination tablet, which is a tablet of 100 mg glucokinase activator (preferably, HMS5552 or an isotope labeled analogue or a pharmaceutically acceptable salt thereof)/1 mg repaglinide tablet) comprises the components with the following amounts (by weight): about 100 mg of the glucokinase activator (preferably, HMS5552 or an isotope labeled analogue or a pharmaceutically acceptable salt thereof); about 1 mg of repaglinide; about 0-90% of optional filler(s); about 1-25% of binder(s); about 1-15% of disintegrant(s); about 0.5-3% of lubricant(s); about 0-0.5% of glidant(s) and about 0-5% of coating agent(s); wherein the above-mentioned glucokinase activator is in the form of a solid dispersion as described above.

In one embodiment, the pharmaceutical combination, pharmaceutical composition, or pharmaceutical formulation (preferably, a fixed dose combination tablet, which is a tablet of 25 mg glucokinase activator (preferably, HMS5552 or an isotope labeled analogue or a pharmaceutically acceptable salt thereof)/2 mg repaglinide) comprises the components with the following amounts (by weight): about 25 mg of the glucokinase activator (preferably, HMS5552 or an isotope labeled analogue or a pharmaceutically acceptable salt thereof); about 2 mg of repaglinide; about 0-90% of optional filler(s); about 1-25% of binder(s); about 1-15% of disintegrant(s); about 0.5-3% of lubricant(s); about 0-0.5% of glidant(s) and about 0-5% of coating agent(s); wherein the above-mentioned glucokinase activator is in the form of a solid dispersion as described above.

In one embodiment, the pharmaceutical combination, pharmaceutical composition, or pharmaceutical formulation (preferably, a fixed dose combination tablet, which is a tablet of 50 mg glucokinase activator (preferably, HMS5552 or an isotope labeled analogue or a pharmaceutically acceptable salt thereof)/2 mg repaglinide) comprises the components with the following amounts (by weight): about 50 mg of the glucokinase activator (preferably, HMS5552 or an isotope labeled analogue or a pharmaceutically acceptable salt thereof); about 2 mg of repaglinide; about 0-90% of optional filler(s); about 1-25% of binder(s); about 1-15% of disintegrant(s); about 0.5-3% of lubricant(s); about 0-0.5% of glidant(s) and about 0-5% of coating agent(s); wherein the above-mentioned glucokinase activator is in the form of a solid dispersion as described above.

In one embodiment, the pharmaceutical combination, pharmaceutical composition, or pharmaceutical formulation (preferably, a fixed dose combination tablet, which is a tablet of 75 mg glucokinase activator (preferably, HMS5552 or an isotope labeled analogue or a pharmaceutically acceptable salt thereof)/2 mg repaglinide) comprises the components with the following amounts (by weight): about 75 mg of the glucokinase activator (preferably, HMS5552 or an isotope labeled analogue or a pharmaceutically acceptable salt thereof); about 2 mg of repaglinide; about 0-90% of optional filler(s); about 1-25% of binder(s); about 1-15% of disintegrant(s); about 0.5-3% of lubricant(s); about 0-0.5% of glidant(s) and about 0-5% of coating agent(s); wherein the above-mentioned glucokinase activator is in the form of a solid dispersion as described above.

In one embodiment, the pharmaceutical combination, pharmaceutical composition, or pharmaceutical formulation (preferably, a fixed dose combination tablet, which is a tablet of 100 mg glucokinase activator (preferably, HMS5552 or an isotope labeled analogue or a pharmaceutically acceptable salt thereof)/2 mg repaglinide) comprises the components with the following amounts (by weight): about 100 mg of the glucokinase activator (preferably, HMS5552 or an isotope labeled analogue or a pharmaceutically acceptable salt thereof); about 2 mg of repaglinide; about 0-90% of optional filler(s); about 1-25% of binder(s); about 1-15% of disintegrant(s); about 0.5-3% of lubricant(s); about 0-0.5% of glidant(s) and about 0-5% of coating agent(s); wherein the above-mentioned glucokinase activator is in the form of a solid dispersion as described above.

In one embodiment, the above-mentioned pharmaceutical combination, pharmaceutical composition or pharmaceutical formulation (preferably, a fixed dose combination formulation) further comprises other excipients, wherein the other excipients include but are not limited to one or a mixture of diluents, flavoring agents (flavors), sweetening agents, and coloring agents.

In one embodiment, the pharmaceutical combination, pharmaceutical composition or pharmaceutical formulation (preferably, a fixed dose combination formulation) disclosed herein contains optionally one or more fillers (diluents). Examples of fillers include, but are not limited to, cellulose derivatives such as microcrystalline cellulose or lignocellulose (including microcrystalline cellulose and silicified microcrystalline cellulose), lactose, anhydrous lactose or lactose monohydrate, sucrose, starch, pregelatinized starch, dextrose, mannitol (including mannitol Pearlitol SD 200), fructose, xylitol, sorbitol, corn starch, modified corn starch, inorganic salts such as calcium carbonate, calcium phosphate, dicalcium phosphate, calcium sulfate, dextrin/glucose binder, maltodextrin, compressible sugar and other known compatibilizers or fillers/or a mixture of two or more of them.

Examples of preferable fillers (diluents) include microcrystalline cellulose (MCC), silicified microcrystalline cellulose (SMCC), lactose, mannitol, sorbitol, calcium dihydrogen phosphate (dihydrate), corn starch, pregelatinized starch and powdered cellulose. Other preferable fillers (diluents) are microcrystalline cellulose and silicified microcrystalline cellulose. Microcrystalline cellulose can be obtained from several suppliers, including Avicel PH 101, Avicel PH 102, Avicel PH 103, Avicel PH 105, and Avicel PH 200 manufactured by FMC Corporation.

In one embodiment, the pharmaceutical combination, pharmaceutical composition or pharmaceutical formulation (preferably, a fixed dose combination formulation) disclosed herein contains optionally one or more binders. Examples include, but are not limited to, carboxymethylcellulose (including sodium carboxymethylcellulose), hydroxypropyl cellulose (including hydroxypropyl cellulose EXF), corn starch, pregelatinized starch, modified corn starch, polyvinyl pyrrolidone (PVP), hydroxypropylmethyl cellulose (HPMC) (including hydroxypropylmethyl cellulose 2208), lactose, sucrose, gum arabic, ethylcellulose, cellulose acetate and wax binders such as carnauba wax, paraffin wax, cetyl wax, polyethylene or microcrystalline wax and other conventional binder and/or a mixture of two or more of them. Further, in addition to the above binders, binders suitable for use in the present disclosure include, but are not limited to, alginic acid, microcrystalline cellulose, dextrin, gelatin, amylopectin, liquid glucose, guar gum, methylcellulose, polyethylene oxide, povidone and syrup, and the combination of them.

Preferable embodiments of the binder include hydroxypropyl cellulose (HPC), hydroxypropyl methyl cellulose (HMPC), polyvinylpyrrolidone (Povidone), hydroxyethyl cellulose, starch 1500 and Polyvidon. Other preferable binders are hydroxypropyl cellulose, hydroxypropyl methyl cellulose and polyvinylpyrrolidone.

In one embodiment, the above-mentioned pharmaceutical combination, pharmaceutical composition or pharmaceutical formulation (preferably, a fixed dose combination formulation) contains optionally one or more disintegrants. Examples of disintegrants suitable for use in the present disclosure include, but are not limited to, croscarmellose sodium, crospovidone, lactose, sucrose, starch, potato starch, pregelatinized starch, corn starch, sodium carboxymethyl starch, sodium starch glycolate, microcrystalline cellulose, light silicic acid anhydride, low-substituted hydroxypropyl cellulose and other known disintegrants.

In one embodiment, the disintegrant is selected from one or more of modified starch, modified cellulose polymer or polycarboxylic acid, specifically selected from the group consisting of croscarmellose sodium, crospovidone, sodium starch glycolate, polacrilin potassium and CMC Calcium. In one embodiment, the disintegrant is crospovidone. In another embodiment, the disintegrant is sodium starch glycolate. In another embodiment, the disintegrant is croscarmellose sodium. Croscarmellose sodium NF type A is available in the market under the trade name "Ac-di-sol".

In one embodiment, the above-mentioned pharmaceutical combination, pharmaceutical composition or pharmaceutical formulation (preferably, a fixed dose combination formulation) contains one or more lubricants. Examples of lubricants suitable for use in the present disclosure include, but are not limited to, magnesium stearate, zinc stearate, calcium stearate, talc, carnauba wax, stearic acid, palmitic acid, sodium stearyl fumarate, sodium lauryl sulphate, glyceryl palmitate stearate, palmitic acid, myristic acid and hydrogenated vegetable oils (including hydrogenated castor oil) and fats and other known lubricants and/or a mixture of two or more of them.

In one embodiment, embodiments of the lubricant include magnesium stearate, calcium stearate, stearic acid, sodium stearyl fumarate, hydrogenated castor oil, and a mixture thereof. Another preferable lubricant is magnesium stearate, or sodium stearyl fumarate, or a mixture thereof.

In one embodiment, the above-mentioned pharmaceutical combination, pharmaceutical composition or pharmaceutical formulation (preferably, a fixed dose combination formulation) contains one or more glidants and/or anti-adherents. Examples of glidants and/or anti-adherents suitable for use in the present disclosure include, but are not limited to, silicon dioxide, colloidal silicon dioxide, calcium phosphate, magnesium silicate, magnesium trisilicate, talc and other forms of silicon dioxide such as aggregated silicate and hydrated silica gel.

In one embodiment, embodiments of the glidant include colloidal silicon dioxide, calcium phosphate, magnesium silicate, and talc, or a mixture thereof. The preferable glidant is colloidal silicon dioxide.

In one embodiment, the above-mentioned pharmaceutical combination, pharmaceutical composition or pharmaceutical formulation (preferably, a fixed dose combination formulation) may also optionally contain one or more surfactants or wetting agents. The surfactant can be an anionic, cationic or neutral surfactant. The anionic surfactant includes sodium dodecyl sulfate, sodium lauryl sulfonate, sodium oleyl sulfate, and sodium laurate mixed with stearate and talc. The cationic surfactant includes benzalkonium chloride and alkyl trimethyl ammonium bromide. The neutral surfactant includes glycerol monooleate, polyoxyethylene sorbitan fatty acid ester, polyvinyl alcohol and sorbitan ester. Embodiments of the wetting agent include poloxamer, polyoxyethylene alkyl ether, polyoxyethylene castor oil derivative, and polyoxyethylene stearate.

In one embodiment, the above-mentioned pharmaceutical combination, pharmaceutical composition or pharmaceutical formulation (preferably, a fixed dose combination formulation) may also optionally contain an antioxidant to render chemical stability. Examples of the antioxidant suitable for use in the present disclosure include, but are not limited to, tocopherol, ascorbic acid, gallic acid ester, ascorbyl palmitate, butylated hydroxyanisole, butylated hydroxytoluene, thioglycerol, potassium metabisulfite, propionic acid, propyl gallate, sodium ascorbate, sodium bisulfite, sodium metabisulfite and sodium sulfite and a combination thereof.

In one embodiment, the antioxidant is selected from the group consisting of α-tocopherol, γ-tocopherol, δ-tocopherol, extracts from natural sources enriched in tocopherol, L-ascorbic acid and sodium or calcium salt thereof, ascorbyl palmitate, propyl gallate, octyl gallate, lauryl gallate, butylated hydroxytoluene (BHT) and butylated hydroxyanisole (BHA). In one embodiment, the antioxidant is BHT or BHA.

In one embodiment, the preferable formulation of the above-mentioned fixed dose combination formulation is a tablet prepared by a compression method. The tablet may be coated, and preferable examples of coating substrates include sugar coating substrates, water-soluble film coating substrates, enteric film coating substrates, and the like.

Sucrose is used as the sugar coating substrate. In addition, one or more selected from talc powder, precipitated calcium carbonate, gelatin, gum arabic, amylopectin, carnauba wax, and the like can also be used in combination.

Examples of the water-soluble film coating substrate include cellulosic polymers such as hydroxypropyl cellulose, hydroxypropyl methyl cellulose, hydroxyethyl cellulose, methyl hydroxyethyl cellulose, and the like; synthetic polymers such as polyvinyl acetal diethylaminoacetate, aminoalkyl methacrylate copolymer E [Eudragit E (trade name)], polyvinylpyrrolidone, and the like.

Examples of the enteric film coating substrate include cellulosic polymers such as hydroxypropyl methyl cellulose phthalate, hydroxypropyl methyl cellulose acetate succinate, carboxymethyl ethyl cellulose, cellulose acetate phthalate, and the like; acrylic polymer, such as methacrylic acid copolymer L [Eudragit L (trade name)], methacrylic acid copolymer LD [Eudragit L-30D55 (trade name)], methacrylic acid copolymer S [Eudragit S (trade name)], and the like.

Preferable examples of coating additives include: plasticizers such as polyvinyl alcohol (PVA), polyethylene glycol (PEG), propylene glycol, triethyl citrate, castor oil, polysorbate, and the like, or a mixture of two or more of them; opacifiers such as titanium dioxide and the like; coloring agents, dyes and lakes such as iron oxide red (ferric oxide), iron oxide yellow, and the like; and glidants such as talc and the like.

In one embodiment, the tablet may be coated with, for example, a mixture of hydroxypropylcellulose and hydroxypropylmethylcellulose, wherein the mixture contains titanium dioxide and/or other coloring agents, such as iron oxide, dyes and lakes; a mixture of polyvinyl alcohol (PVA) and polyethylene glycol (PEG); or any other suitable immediate-release coating agent. The coating provides taste masking and additional stability to the final tablet. The commercially available coating material is Opadry® such as Opadry 03K12429 which is a pre-formulated powder mixture provided by Colorcon.

In one embodiment, in the above-mentioned pharmaceutical combination, pharmaceutical composition or pharmaceutical formulation (preferably, a fixed dose combination formulation), sweetening agents and/or flavoring agents may also be added as needed.

In one embodiment, the above-mentioned binder is polyvinylpyrrolidone, hydroxypropyl cellulose or hydroxypropyl methyl cellulose, the above-mentioned filler is microcrystalline cellulose, silicified microcrystalline cellulose, lactose, calcium dihydrogen phosphate, mannitol, corn starch or pregelatinized starch, the above-mentioned disintegrant is croscarmellose sodium, crospovidone or sodium starch glycolate, the above-mentioned lubricant is magnesium stearate or sodium stearyl fumarate, and the above-mentioned glidant is colloidal silicon dioxide.

In one embodiment, the above-mentioned binder is hydroxypropyl cellulose, the above-mentioned filler is microcrystalline cellulose, silicified microcrystalline cellulose or lactose, the above-mentioned disintegrant is croscarmellose sodium, crospovidone or sodium starch glycolate, the above-mentioned lubricant is magnesium stearate or sodium stearyl fumarate, and the above-mentioned glidant is colloidal silicon dioxide.

In one embodiment, the above-mentioned binder is polyvinylpyrrolidone, the above-mentioned filler is microcrystalline cellulose or silicified microcrystalline cellulose, the above-mentioned disintegrant is croscarmellose sodium or crospovidone, the above-mentioned lubricant is magnesium stearate or sodium stearyl fumarate, and the above-mentioned glidant is colloidal silicon dioxide.

In one embodiment, the above-mentioned binder is hydroxypropyl methyl cellulose, the above-mentioned filler is microcrystalline cellulose, silicified microcrystalline cellulose or lactose, the above-mentioned disintegrant is croscarmellose sodium, crospovidone or sodium starch glycolate, the above-mentioned lubricant is magnesium stearate or sodium stearyl fumarate, and the above-mentioned glidant is colloidal silicon dioxide.

In one embodiment, the above-mentioned binder is hydroxypropyl cellulose, the above-mentioned filler is microcrystalline cellulose, silicified microcrystalline cellulose or lactose, the above-mentioned disintegrant is croscarmellose sodium, and the above-mentioned lubricant is magnesium stearate or sodium stearyl fumarate.

In one embodiment, the above-mentioned binder is polyvinylpyrrolidone, the above-mentioned lubricant is magnesium stearate, and the above-mentioned glidant is colloidal silicon dioxide.

Preparation Method

In one embodiment, the pharmaceutical composition or fixed dose combination formulation disclosed herein is prepared by wet granulation (high shear and/or fluidized bed). The granulation is a method in which binder(s) is added into a solvent to prepare a binder solution, and then added or directly added into a granulator to prepare wet granules. The wet granulation method includes the steps of:

(1) adding an active pharmaceutical ingredient glucokinase activator (preferably, HMS5552) and a partner drug (preferably, glimepiride or repaglinide) into a granulator;

(2) adding optional filler(s) (e.g., microcrystalline cellulose, silicified microcrystalline cellulose, or lactose) into the mixture obtained in step (1);

(3) adding optional disintegrant(s) (e.g., croscarmellose sodium, crospovidone, or sodium starch glycolate) into the mixture obtained in step (1) or (2);

(4) for high-shear granulation, adding binder(s) (e.g., hydroxypropyl cellulose, polyvinylpyrrolidone or hydroxypropyl methyl cellulose) into pure water to prepare a binder solution, and then adding it into a granulator for granulation with stirring. For fluidized bed granulation, two active pharmaceutical ingredients are added into a fluidized bed, and a binder solution that is an aqueous solution prepared from binder(s) and pure water is sprayed into the fluidized bed by compressed air;

(5) sizing the obtained wet granules in a suitable mill to obtain wet granules of suitable size;

(6) for granules prepared by high-shear granulation, drying with a tray in an oven or drying in a fluidized bed dryer; and for granules obtained by granulating in a fluidized bed, drying in a fluidized bed;

(7) sizing the granules on a suitable grinder to obtain dry granules of suitable size;

(8) in a suitable mixer, adding optional filler(s) (diluent(s), such as microcrystalline cellulose) and optional disintegrant(s) (e.g., croscarmellose sodium), and mixing with the dry granules;

(9) adding lubricant(s) (e.g., magnesium stearate and sodium stearyl fumarate) into the mixture in step (8);

(10) adding optional glidant(s) (e.g., colloidal silicon dioxide) into the mixture in step (9);

(11) filling the mixture of lubricated granules in step (9) or (10) into vials, pouches or capsules, or compressing it into a tablet with a desired shape; and

(12) optionally, film-coating the obtained tablets.

In another embodiment, the pharmaceutical composition disclosed herein is prepared by wet granulation (high shear and/or fluidized bed). The granulation is a method in which binder(s) and a second active ingredient are added into a solvent to prepare a binder solution (or suspension), and then added into a granulator to prepare wet granules. The wet granulation method includes the steps of:

(1) adding the active pharmaceutical ingredient glucokinase activator (preferably, HMS5552) into a granulator;

(2) adding optional filler(s) (e.g., microcrystalline cellulose, silicified microcrystalline cellulose, or lactose) into the mixture in step (1);

(3) adding optional disintegrant(s) (e.g., croscarmellose sodium, crospovidone, or sodium starch glycolate) into the mixture obtained in step (1) or (2);

(4) for high-shear granulation, adding binder(s) (e.g., hydroxypropyl cellulose, polyvinylpyrrolidone or hydroxypropyl methyl cellulose) into a solvent for uniform dispersion or dissolution, and then adding the second active ingredient (preferably, glimepiride or repaglinide) in a formulated amount for dispersion or dissolution, so as to form a uniform binder system. The system is added into a granulator for granulation with stirring. For fluidized bed granulation, an active pharmaceutical ingredient such as HMS5552 is added into a fluidized bed, and a binder system that is a solution or suspension prepared by binder(s) and pure water or an organic solvent (e.g., ethanol) is sprayed into the fluidized bed by compressed air;
(5) sizing the obtained wet granules in a suitable mill to obtain wet granules of suitable size;
(6) for granules prepared by high-shear granulation, drying with a tray in an oven or drying in a fluidized bed dryer; and for granules obtained by granulating in a fluidized bed, drying in a fluidized bed;
(7) sizing the granules on a suitable grinder to obtain dry granules of suitable size;
(8) in a suitable mixer, adding optional filler(s) (diluent, such as microcrystalline cellulose) and optional disintegrant(s) (e.g., croscarmellose sodium), and mixing with the dry granules;
(9) adding lubricant(s) (e.g., magnesium stearate and sodium stearyl fumarate) into the mixture in step (8);
(10) optionally, adding optional glidant(s) (e.g., colloidal silicon dioxide) into the mixture in step (9);
(11) filling the mixture of lubricated granules in (9) or (10) into vials, pouches or capsules, or compressing it into a tablet with a desired shape; and
(12) optionally, film-coating the obtained tablets.

The dry processing (direct compression or dry granulation) method includes the steps of:
(1) adding the active pharmaceutical ingredient glucokinase activator (preferably, HMS5552) and the partner drug (preferably, glimepiride or repaglinide) into a mixing tank;
(2) adding optional filler(s) (e.g., microcrystalline cellulose, silicified microcrystalline cellulose, or lactose) into the mixture in step (1);
(3) adding optional binder(s) (e.g., hydroxypropyl cellulose, polyvinylpyrrolidone or hydroxypropyl methyl cellulose) into the mixture obtained in step (1) or (2);
(4) adding lubricant(s) or glidant(s) into the mixture in step (3), and mixing;
(5) filling the mixture in step (4) into vials, pouches or capsules, compressing the mixture in step (4) into a tablet with a desired shape, or processing the mixture in step (4) by a roller compressor;
(6) mixing the mixture in step (3) in advance, and then rolled with a roller if processing the mixture in step (4) by a roller compressor; if necessary, sizing the granules on a suitable grinder to obtain granules of the required size;
(7) in a suitable mixer, adding optional diluent(s) to the granules obtained in step (6) to improve the compression performance;
(8) adding optional disintegrant(s) (e.g., croscarmellose sodium, crospovidone, or sodium starch glycolate) into the mixture in step (7);
(9) adding optional lubricant(s) or glidant(s) into the mixture in step (8);
(10) filling the mixture of lubricated granules in step (9) or (10) into vials, pouches or capsules, or compressing it into a tablet with a desired shape; and
(11) optionally, film-coating the tablets obtained in step (5) or step (10).

In one embodiment disclosed herein, the glucokinase activator in the pharmaceutical combination, pharmaceutical composition or fixed dose combination formulation disclosed herein is in the form of a solid dispersion, which can be prepared by a method selected from the group consisting of spray drying method, fluidized bed drying method, solvent method, melt extrusion method and the like.

One embodiment disclosed herein is a method of preparing a solid dispersion of a glucokinase activator by a spray drying method, which includes the steps of:
(1) formulating a spray drying solution, including dissolving a polymer carrier and a glucokinase activator (preferably, HMS5552) in a solvent;
(2) spray drying, including controlling the temperature of the inlet air, the amount of the inlet air, the flow rate and pressure of the atomized airflow, the spraying speed of the solution, and the like.

In the embodiment disclosed herein, the solvent used in the preparation of the solid dispersion of the glucokinase activator includes but is not limited to alkanols, esters, nitriles, cycloalkanes, aromatic hydrocarbons, ketones and the like. Specifically, the solvent is selected from the group consisting of anhydrous ethanol, methanol, isopropanol, ethyl acetate, acetone, acetonitrile, isobutanol, n-hexane, benzene and toluene. The solvent can be a single solvent, a mixed solvent, or a mixture of an organic solvent and water.

Methods and Uses for Treating and/or Preventing Diseases

Another embodiment disclosed herein relates to a method or use of a composition or formulation (preferably, a fixed dose combination pharmaceutical composition or a fixed dose combination formulation) comprising a glucokinase activator disclosed herein for the treatment and/or prevention of the following diseases and medical disorders, especially one or more diseases selected from the group consisting of type I diabetes, type II diabetes, impaired glucose tolerance, impaired fasting blood glucose, and hyperglycemia, including administering to a subject a therapeutically effective amount of the composition or preparation (preferably, a fixed dose combination pharmaceutical composition or a fixed dose combination formulation) disclosed herein:
  preventing, slowing the progression of, delaying or treating a metabolic disorder selected from the group consisting of type 1 diabetes mellitus, type 2 diabetes mellitus, impaired glucose tolerance, impaired fasting blood glucose, hyperglycemia, postprandial hyperglycemia, overweight, obesity and metabolic syndrome; or
  improving glycemic control and/or for reducing of fasting plasma glucose, of postprandial plasma glucose and/or of glycosylated hemoglobin HbA1c; or
  preventing, slowing, delaying or reversing progression from impaired glucose tolerance, insulin resistance and/or from metabolic syndrome to type 2 diabetes mellitus; or
  preventing, slowing the progression of, delaying or treating of a condition or disorder selected from the group consisting of complications of diabetes mellitus such as cataracts and micro- and macrovascular diseases, such as nephropathy, retinopathy, neuropathy, learning and memory dysfunction, neurodegenerative or cognitive disorders, cardio- or cerebrovascular diseases, tissue ischaemia, diabetic foot or ulcus, arteriosclerosis, hypertension, endothelial dysfunction, myocardial infarction, accute coronary syndrome, unstable angina pectoris, stable angina pectoris, stroke, peripheral arterial occlusive disease, cardiomyopathy, heart failure, heart rhythm disorders and vascular restenosis; or
  reducing body weight and/or body fat or preventing an increase in body weight and/or body fat or facilitating a reduction in body weight and/or body fat; or preventing, slowing, delaying or treating the degeneration of pancreatic beta cells and/or the decline of the functionality of pancreatic beta cells and/or for improving and/or restoring or protecting the functionality of pancreatic beta cells and/or restoring the functionality of pancreatic insulin secretion; or for preventing, slowing, delaying or treating diseases or conditions attributed to an abnormal accumulation of liver or ectopic fat; or maintaining and/or improving the insulin sensitivity and/or for treating or preventing hyperinsulinemia and/or insulin resistance; or for preventing, slowing progression of, delaying, or treating new onset diabetes after transplantation (NODAT) and/or post-transplant metabolic syndrome (PTMS); or for preventing, delaying, or reducing NODAT and/or PTMS associated complications including micro- and macrovascular diseases and events, graft rejection, infection, and death; or for treating hyperuricemia and hyperuricemia associated conditions; or for preventing, slowing, delaying or treating maturity-onset diabetes of the young (MODY), and diseases associated with islet dysfunction.

The present disclosure also provides a method for the treatment of type II diabetes by orally administering a therapeutically effective amount of a pharmaceutical composition or formulation (preferably, a fixed dose combination pharmaceutical composition or a fixed dose combination formulation) comprising a glucokinase activator and a partner drug disclosed herein to a subject in need of the treatment. In one embodiment, the subject in need of the treatment is a human. In another embodiment, the pharmaceutical composition is in the form of a tablet. The composition or formulation (preferably, a fixed dose combination pharmaceutical composition or a fixed dose combination formulation) comprising a glucokinase activator disclosed herein can be administered once a day (QD), twice a day (BID) or three times a day (TID).

Specifically, the present disclosure relates to the following specific embodiments.

Embodiment I—Glucokinase Activator+K-ATP Channel Blocker (e.g. Glimepiride)

Solution 1. A pharmaceutical combination, a pharmaceutical composition, or a fixed dose combination formulation, comprising:
(a) a glucokinase activator, which is a compound represented by the following formulae, or a pharmaceutically acceptable salt, an isotope labeled analogue, a crystalline form, a hydrate, a solvate, or a diastereomeric or enantiomeric form thereof,

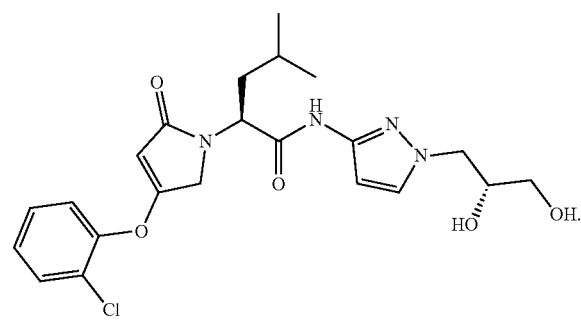
HMS5552

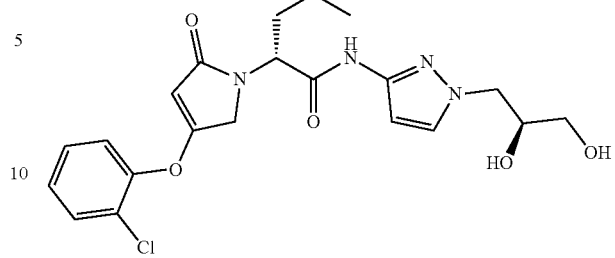

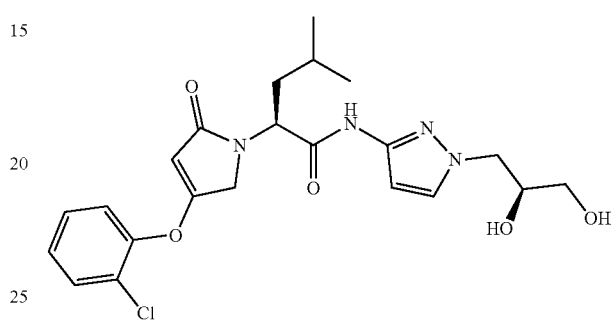

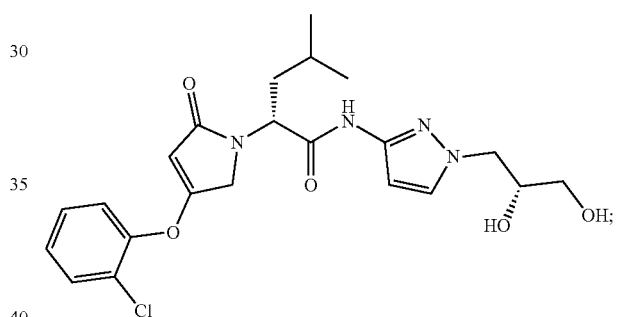

(b) a K-ATP channel blocker; and
(c) one or more excipients;
wherein the above-mentioned drugs (a) and (b) are used simultaneously, separately or sequentially.

Solution 2. The pharmaceutical combination, pharmaceutical composition, or fixed dose combination formulation of solution 1, wherein the weight ratio of the glucokinase activator to the K-ATP channel blocker is about 400:1 to 10:1, preferably about 100:1 to 25:2, or more preferably about 25:2, about 25:1, about 50:1, about 75:2, about 75:1, or about 100:1.

Solution 3. The pharmaceutical combination, pharmaceutical composition, or fixed dose combination formulation of solution 1 or 2, wherein the glucokinase activator is about 1-99% by weight; and the K-ATP channel blocker is about 0.1-15% by weight.

Solution 4. The pharmaceutical combination, pharmaceutical composition, or fixed dose combination formulation of any one of solutions 1-3, wherein the glucokinase activator is the compound HMS5552 represented by the following formula, or a pharmaceutically acceptable salt, an isotope labeled analogue, a crystalline form, a hydrate, a solvate, or a diastereomeric or enantiomeric form thereof,

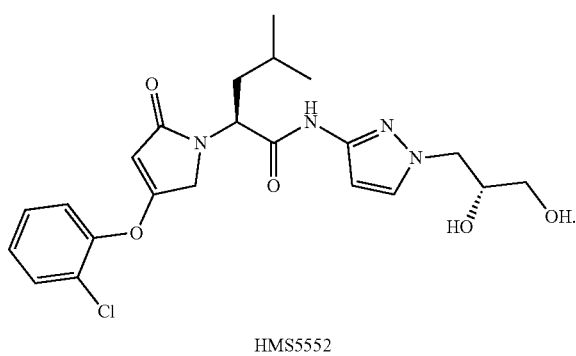 [SMILES: CC(C)C[C@@H](C(=O)Nc1ccn(C[C@@H](O)CO)n1)N1CC(Oc2ccccc2Cl)=CC1=O]

HMS5552

Solution 5. The pharmaceutical combination, pharmaceutical composition, or fixed dose combination formulation of any one of solutions 1-4, wherein the glucokinase activator is in the form of a solid dispersion.

Solution 6. The pharmaceutical combination, pharmaceutical composition, or fixed dose combination formulation of solution 5, wherein the glucokinase activator is in the form of a solid dispersion containing a polymer carrier, and the polymer carrier is a methacrylic acid copolymer of type A (an anionic copolymer of methacrylic acid and methyl methacrylate (1:1)), preferably Eudragit, or more preferably Eudragit L100.

Solution 7. The pharmaceutical combination, pharmaceutical composition, or fixed dose combination formulation of solution 6, wherein the weight ratio of the glucokinase activator to the polymer carrier is about 1:10 to 10:1, preferably about 1:9 to 9:1, about 1:4 to 4:1, about 3:7 to 7:3, about 2:3 to 3:2, about 3:4 to 4:3, about 4:5 to 5:4 or about 5:6 to 6:5, or more preferably about 1:1, about 2:3, about 3:4, about 4:5 or about 5:6 or any range therebetween.

Solution 8. The pharmaceutical combination, pharmaceutical composition, or fixed dose combination formulation of any one of solutions 1-7, wherein the K-ATP channel blocker is selected from the group consisting of sulfonylurea secretagogues including glibenclamide, glipizide, gliclazide, gliquidone and glimepiride, and a pharmaceutically acceptable salt thereof; or selected from the group consisting of non-sulfonylurea insulin secretagogues including repaglinide and nateglinide, and a pharmaceutically acceptable salt thereof.

Solution 9. The pharmaceutical combination, pharmaceutical composition, or fixed dose combination formulation of any one of solutions 1-8, wherein the glucokinase activator is present in a dose (preferably, a unit dose) ranging from about 1 mg to about 200 mg, or preferably about 25 mg to about 100 mg, preferably, wherein the dose (preferably, a unit dose) of the glucokinase activator is about 25 mg, about 50 mg, about 75 mg, or about 100 mg.

Solution 10. The pharmaceutical combination, pharmaceutical composition, or fixed dose combination formulation of any one of solutions 1-9, wherein the K-ATP channel blocker is present in a dose (preferably, a unit dose) ranging from about 0.1 mg to about 10 mg, or preferably about 1 mg to about 5 mg, preferably, wherein the dose (preferably, a unit dose) of the K-ATP channel blocker is about 0.1 mg, about 0.2 mg, about 0.5 mg, about 1 mg, about 1.5 mg, about 2 mg, about 4 mg or about 5 mg, or still preferably about 1 mg or about 2 mg; and preferably, the K-ATP channel blocker is glimepiride or repaglinide.

Solution 11. The pharmaceutical combination, pharmaceutical composition, or fixed dose combination formulation of any one of solutions 1-10, wherein the one or more excipients are selected from the group consisting of binders, fillers, disintegrants, lubricants, glidants, surfactants, wetting agents, antioxidants, flavoring agents, sweetening agents, coloring agents and coating agents.

Solution 12. The pharmaceutical combination, pharmaceutical composition, or fixed dose combination formulation of any one of solutions 1-11, which is a tablet.

Solution 13. The pharmaceutical combination, pharmaceutical composition, or fixed dose combination formulation of solution 12, which is a coated tablet.

Solution 14. The pharmaceutical combination, pharmaceutical composition, or fixed dose combination formulation of solution 13, wherein the coated tablet is a film-coated tablet, and the film-coating agent comprises:
film-coating substrate(s), such as hypromellose, hydroxypropyl methyl cellulose, or a mixture thereof;
optional plasticizer(s), such as polyvinyl alcohol, polyethylene glycol, propylene glycol, polysorbate, or a mixture thereof;
optional coloring agent(s), such as iron oxide red, iron oxide yellow, or a mixture thereof; optional opacifier(s), such as titanium dioxide, and
optional glidant(s).

Solution 15. The pharmaceutical combination, pharmaceutical composition, or fixed dose combination formulation of solution 14, wherein the coated tablet is a film-coated tablet, and the film-coating agent is Opadry.

Solution 16. The pharmaceutical combination, pharmaceutical composition, or fixed dose combination formulation of any one of solutions 1-15, comprising (by weight): about 1-99% of the glucokinase activator (preferably, HMS5552 or an isotope labeled analogue or a pharmaceutically acceptable salt thereof), preferably HMS5552, preferably a solid dispersion of HMS5552, preferably a solid dispersion containing HMS5552 and a polymer carrier, or preferably a solid dispersion containing about 1:1 of HMS5552 and Eudragit L100;
about 0.1-15% of glimepiride;
about 0-85% of filler(s);
about 1-25% of binder(s);
about 0-15% of disintegrant(s);
about 0.1-10% of lubricant(s);
about 0-3% of glidant(s); and
about 0-3% of coating agent(s).

Solution 17. The pharmaceutical combination, pharmaceutical composition, or fixed dose combination formulation of solution 16, comprising (by weight):
about 1 to 50% of the glucokinase activator (preferably, HMS5552 or an isotope labeled analogue or a pharmaceutically acceptable salt thereof), preferably HMS5552, preferably a solid dispersion of HMS5552, preferably a solid dispersion containing HMS5552 and a polymer carrier, or preferably a solid dispersion containing about 1:1 of HMS5552 and Eudragit L100;
about 0.1-8% of glimepiride;
about 0-90% of filler(s);
about 1-10% of binder(s);
about 1-10% of disintegrant(s);
about 0.1-5% of lubricant(s);
about 0-3% of glidant(s); and
about 0-3% of coating agent(s).

Solution 18. The pharmaceutical combination, pharmaceutical composition, or fixed dose combination formulation of solution 16, wherein the doses (preferably, unit doses) of the active ingredients are (by weight):

about 25 mg, about 50 mg, about 75 mg or about 100 mg of the glucokinase activator, or preferably HMS5552;
about 1 mg, about 2 mg or about 4 mg of glimepiride;
about 0-85% of filler(s);
about 1-25% of binder(s);
about 0-15% of disintegrant(s);
about 0.1-10% of lubricant(s);
about 0-3% of glidant(s); and
about 0-3% of coating agent(s).

Solution 19. The pharmaceutical combination, pharmaceutical composition, or fixed dose combination formulation (the fixed dose combination formulation is preferably a tablet of 50 mg HMS5552/1 mg glimepiride) of solution 18, comprising the components with the following amounts (by weight):
   about 50 mg of HMS5552, preferably a solid dispersion of HMS5552, preferably a solid dispersion containing HMS5552 and a polymer carrier, or preferably a solid dispersion containing about 1:1 of HMS5552 and Eudragit L100;
   about 1 mg of glimepiride;
   about 0-80% of filler(s);
   about 2-8% of binder(s);
   about 1-5% of disintegrant(s);
   about 0.5-3% of lubricant(s);
   about 0-0.5% of glidant(s); and
   about 0-5% of coating agent(s).

Solution 20. The pharmaceutical combination, pharmaceutical composition, or fixed dose combination formulation (the fixed dose combination formulation is preferably a tablet of 75 mg HMS5552/1 mg glimepiride) of solution 18, comprising the components with the following amounts (by weight):
   about 75 mg of HMS5552, preferably a solid dispersion of HMS5552, preferably a solid dispersion containing HMS5552 and a polymer carrier, or preferably a solid dispersion containing about 1:1 of HMS5552 and Eudragit L100;
   about 1 mg of glimepiride;
   about 0-80% of filler(s);
   about 2-8% of binder(s);
   about 1-5% of disintegrant(s);
   about 0.5-3% of lubricant(s);
   about 0-0.5% of glidant(s); and
   about 0-5% of coating agent(s).

Solution 21. The pharmaceutical combination, pharmaceutical composition, or fixed dose combination formulation (the fixed dose combination formulation is preferably a tablet of 100 mg HMS5552/1 mg glimepiride) of solution 18, comprising the components with the following amounts (by weight):
   about 100 mg of HMS5552, preferably a solid dispersion of HMS5552, preferably a solid dispersion containing HMS5552 and a polymer carrier, or preferably a solid dispersion containing about 1:1 of HMS5552 and Eudragit L100;
   about 1 mg of glimepiride;
   about 0-80% of filler(s);
   about 2-8% of binder(s);
   about 1-5% of disintegrant(s);
   about 0.5-3% of lubricant(s);
   about 0-0.5% of glidant(s); and
   about 0-5% of coating agent(s).

Solution 22. The pharmaceutical combination, pharmaceutical composition, or fixed dose combination formulation (the fixed dose combination formulation is preferably a tablet of 25 mg HMS5552/2 mg glimepiride) of solution 18, comprising the components with the following amounts (by weight):
   about 25 mg of HMS5552, preferably a solid dispersion of HMS5552, preferably a solid dispersion containing HMS5552 and a polymer carrier, or preferably a solid dispersion containing about 1:1 of HMS5552 and Eudragit L100;
   about 2 mg of glimepiride;
   about 0-80% of filler(s);
   about 2-8% of binder(s);
   about 1-5% of disintegrant(s);
   about 0.5-3% of lubricant(s);
   about 0-0.5% of glidant(s); and
   about 0-5% of coating agent(s).

Solution 23. The pharmaceutical combination, pharmaceutical composition, or fixed dose combination formulation (the fixed dose combination formulation is preferably a tablet of 50 mg HMS5552/2 mg glimepiride) of solution 18, comprising the components with the following amounts (by weight):
   about 50 mg of HMS5552, preferably a solid dispersion of HMS5552, preferably a solid dispersion containing HMS5552 and a polymer carrier, or preferably a solid dispersion containing about 1:1 of HMS5552 and Eudragit L100;
   about 2 mg of glimepiride;
   about 0-80% of filler(s);
   about 2-8% of binder(s);
   about 1-5% of disintegrant(s);
   about 0.5-3% of lubricant(s);
   about 0-0.5% of glidant(s); and
   about 0-5% of coating agent(s).

Solution 24. The pharmaceutical combination, pharmaceutical composition, or fixed dose combination formulation (the fixed dose combination formulation is preferably a tablet of 75 mg HMS5552/2 mg glimepiride) of solution 18, comprising the components with the following amounts (by weight):
   about 75 mg of HMS5552, preferably a solid dispersion of HMS5552, preferably a solid dispersion containing HMS5552 and a polymer carrier, or preferably a solid dispersion containing about 1:1 of HMS5552 and Eudragit L100;
   about 2 mg of glimepiride;
   about 0-80% of filler(s);
   about 2-8% of binder(s);
   about 1-5% of disintegrant(s);
   about 0.5-3% of lubricant(s);
   about 0-0.5% of glidant(s); and
   about 0-5% of coating agent(s).

Solution 25. The pharmaceutical combination, pharmaceutical composition, or fixed dose combination formulation of solution 18, comprising about 100 mg of the solid dispersion, about 1.00 mg of glimepiride, about 129.00 mg of microcrystalline cellulose, about 7.50 mg of hydroxypropyl cellulose, about 7.50 mg of croscarmellose sodium, about 2.50 mg of sodium dodecyl sulfate, about 2.50 mg of magnesium stearate and about 7.50 mg of Opadry, wherein the solid dispersion contains about 1:1 of HMS5552 and Eudragit L100, and contains about 50 mg of HMS5552.

Solution 26. The pharmaceutical combination, pharmaceutical composition, or fixed dose combination formulation of solution 18, comprising about 150 mg of the solid dispersion, about 1.00 mg of glimepiride, about 79.00 mg of microcrystalline cellulose, about 7.50 mg of hydroxypropyl cellulose, about 7.50 mg of croscarmellose sodium, about 2.50 mg of sodium dodecyl sulfate, about 2.50 mg of magnesium stearate, and about 7.50 mg of Opadry, wherein the solid dispersion contains about 1:1 of HMS5552 and Eudragit L100, and contains about 75 mg of HMS5552.

Solution 27. The pharmaceutical combination, pharmaceutical composition, or fixed dose combination formulation of solution 18, comprising about 200 mg of the solid dispersion, about 1.00 mg of glimepiride, about 29.00 mg of microcrystalline cellulose, about 7.50 mg of hydroxypropyl cellulose, about 7.50 mg of croscarmellose sodium, about 2.50 mg of sodium dodecyl sulfate, about 2.50 mg of magnesium stearate, and about 7.50 mg of Opadry, wherein the solid dispersion contains about 1:1 of HMS5552 and Eudragit L100, and contains about 100 mg of HMS5552.

Solution 28. The pharmaceutical combination, pharmaceutical composition, or fixed dose combination formulation of solution 18, comprising about 100 mg of the solid dispersion, about 2.00 mg of glimepiride, about 128.00 mg of microcrystalline cellulose, about 7.50 mg of hydroxypropyl cellulose, about 7.50 mg of croscarmellose sodium, about 2.50 mg of sodium dodecyl sulfate, about 2.50 mg of magnesium stearate, and about 7.50 mg of Opadry, wherein the solid dispersion contains about 1:1 of HMS5552 and Eudragit L100, and contains about 50 mg of HMS5552.

Solution 29. The pharmaceutical combination, pharmaceutical composition, or fixed dose combination formulation of solution 18, comprising about 150 mg of the solid dispersion, about 2.00 mg of glimepiride, about 78.00 mg of microcrystalline cellulose, about 7.50 mg of hydroxypropyl cellulose, about 7.50 mg of croscarmellose sodium, about 2.50 mg of sodium dodecyl sulfate, about 2.50 mg of magnesium stearate and about 7.50 mg of Opadry, wherein the solid dispersion contains about 1:1 of HMS5552 and Eudragit L100, and contains about 75 mg of HMS5552.

Solution 30. The pharmaceutical combination, pharmaceutical composition, or fixed dose combination formulation of solution 18, comprising about 50 mg of the solid dispersion, about 2.00 mg of glimepiride, about 136.00 microcrystalline cellulose, and about 4.00 mg of hydroxypropyl cellulose, about 4.00 croscarmellose sodium, about 2.00 mg of sodium dodecyl sulfate, about 2.00 mg of magnesium stearate and about 6.00 mg of Opadry, wherein the solid dispersion contains about 1:1 of HMS5552 and Eudragit L100, and contains about 25 mg of HMS5552.

Solution 31. A method for preparing the pharmaceutical combination, pharmaceutical composition, or fixed dose combination formulation of any one of solutions 1-30, comprising incorporating the active ingredients into one or more excipients for granulation, preferably further filling the obtained granule mixture into a vial, a sachet or a capsule, or compressing it into a tablet with a desired shape; and more preferably, further coating the obtained tablet.

Solution 32. The method for preparing the pharmaceutical combination, pharmaceutical composition, or fixed dose combination formulation according to solution 31, wherein the preparation is carried out by wet granulation (high shear and/or fluidized bed), or by dry processing (direct compression or dry granulation).

Solution 33. The method for preparing the pharmaceutical combination, pharmaceutical composition, or fixed dose combination formulation according to any one of solutions 30-31, wherein the glucokinase activator is prepared in the form of a solid dispersion.

Solution 34. The method for preparing the pharmaceutical combination, pharmaceutical composition, or fixed dose combination formulation according to any one of solutions 30-32, wherein the glucokinase activator and the second or more active ingredients can also be prepared together in the form of a combination solid dispersion (that is, a solid dispersion comprising two or more active ingredients).

Solution 35. The pharmaceutical combination, pharmaceutical composition, or fixed dose combination formulation of any one of solutions 1-30, which is used to prevent, slow the progression of, delay, or treat one or more metabolic disorders selected from the group consisting of: type I diabetes, type II diabetes, maturity-onset diabetes of the young (MODY), impaired glucose tolerance, impaired fasting blood glucose, hyperglycemia, postprandial hyperglycemia, overweight, obesity, hypertension, insulin resistance, diseases associated with islet dysfunction and/or metabolic syndrome; or improve blood glucose control and/or reduce fasting plasma glucose, postprandial plasma glucose and/or glycosylated hemoglobin HbA1c; or prevent, slow, delay, or reverse complications of diabetes mellitus.

Solution 36. A method for preventing, slowing the progression of, delaying, or treating one or more metabolic disorders selected from the group consisting of: type I diabetes, type II diabetes, maturity-onset diabetes of the young (MODY), impaired glucose tolerance, impaired fasting blood glucose, hyperglycemia, postprandial hyperglycemia, overweight, obesity, hypertension, insulin resistance, diseases associated with islet dysfunction and/or metabolic syndrome; or improving blood glucose control and/or reducing fasting plasma glucose, postprandial plasma glucose and/or glycosylated hemoglobin HbA1c; or preventing, slowing, delaying, or reversing complications of diabetes mellitus, comprising administering to a subject a therapeutically effective amount of the pharmaceutical combination, pharmaceutical composition or fixed dose combination formulation of any one of solutions 1-30.

Solution 37. Use of the pharmaceutical combination, pharmaceutical composition or fixed dose combination formulation of any one of solutions 1-30 in the manufacture of a medicament for preventing, slowing the progression of, delaying, or treating one or more metabolic disorders selected from the group consisting of: type I diabetes, type II diabetes, maturity-onset diabetes of the young (MODY), impaired glucose tolerance, impaired fasting blood glucose, hyperglycemia, postprandial hyperglycemia, overweight, obesity, hypertension, insulin resistance, diseases associated with islet dysfunction and/or metabolic syndrome; or improving blood glucose control and/or reducing fasting plasma glucose, postprandial plasma glucose and/or glycosylated hemoglobin HbA1c.

Embodiment II—Glucokinase Activator+K-ATP Channel Blocker (e.g. Repaglinide)

Solution 1. A pharmaceutical combination, a pharmaceutical composition, or a fixed dose combination formulation, comprising:

(a) a glucokinase activator, which is a compound represented by the following formulae, or a pharmaceutically acceptable salt, an isotope labeled analogue, a crystalline form, a hydrate, a solvate, or a diastereomeric or enantiomeric form thereof,

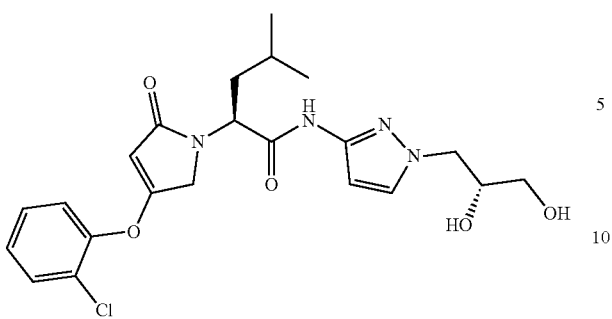

HMS5552

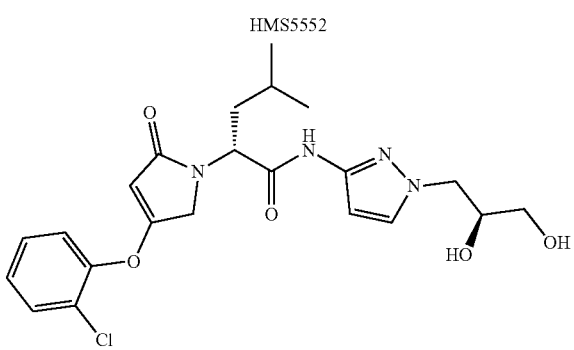

(b) a K-ATP channel blocker; and
(c) one or more excipients;
wherein the above-mentioned drugs (a) and (b) are used simultaneously, separately or sequentially.

Solution 2. The pharmaceutical combination, pharmaceutical composition, or fixed dose combination formulation of solution 1, wherein the weight ratio of the glucokinase activator to the K-ATP channel blocker is about 400:1 to 10:1, preferably about 100:1 to 25:2, or more preferably about 25:2, about 25:1, about 50:1, about 75:2, about 75:1, or about 100:1.

Solution 3. The pharmaceutical combination, pharmaceutical composition, or fixed dose combination formulation of solution 1 or 2, wherein the glucokinase activator is about 1-99% by weight; and the K-ATP channel blocker is about 0.1-8% by weight.

Solution 4. The pharmaceutical combination, pharmaceutical composition, or fixed dose combination formulation of any one of solutions 1-3, wherein the glucokinase activator is the compound HMS5552 represented by the following formula, or a pharmaceutically acceptable salt, an isotope labeled analogue, a crystalline form, a hydrate, a solvate, or a diastereomeric or enantiomeric form thereof,

HMS5552

Solution 5. The pharmaceutical combination, pharmaceutical composition, or fixed dose combination formulation of any one of solutions 1-4, wherein the glucokinase activator is in the form of a solid dispersion.

Solution 6. The pharmaceutical combination, pharmaceutical composition, or fixed dose combination formulation of solution 5, wherein the glucokinase activator is in the form of a solid dispersion containing a polymer carrier, and the polymer carrier is a methacrylic acid copolymer of type A (an anionic copolymer of methacrylic acid and methyl methacrylate (1:1)), preferably Eudragit, or more preferably Eudragit L100.

Solution 7. The pharmaceutical combination, pharmaceutical composition, or fixed dose combination formulation of solution 6, wherein the weight ratio of the glucokinase activator to the polymer carrier is about 1:10 to 10:1, preferably about 1:9 to 9:1, about 1:4 to 4:1, about 3:7 to 7:3, about 2:3 to 3:2, about 3:4 to 4:3, about 4:5 to 5:4 or about 5:6 to 6:5, or more preferably about 1:1, about 2:3, about 3:4, about 4:5 or about 5:6 or any range therebetween.

Solution 8. The pharmaceutical combination, pharmaceutical composition, or fixed dose combination formulation of any one of solutions 1-7, wherein the K-ATP channel blocker is selected from the group consisting of sulfonylurea secretagogues including glibenclamide, glipizide, gliclazide, gliquidone and glimepiride, and a pharmaceutically acceptable salt thereof; or selected from the group consisting of non-sulfonylurea insulin secretagogues including repaglinide and nateglinide, and a pharmaceutically acceptable salt thereof.

Solution 9. The pharmaceutical combination, pharmaceutical composition, or fixed dose combination formulation of any one of solutions 1-8, wherein the glucokinase activator is present in a dose (preferably, a unit dose) ranging from about 1 mg to about 200 mg, or preferably about 25 mg to about 100 mg, preferably, wherein the dose (preferably, a unit dose) of the glucokinase activator is about 25 mg, about 50 mg, about 75 mg, or about 100 mg.

Solution 10. The pharmaceutical combination, pharmaceutical composition, or fixed dose combination formulation of any one of solutions 1-9, wherein the K-ATP channel blocker is present in a dose (preferably, a unit dose) ranging from about 0.1 mg to about 10 mg, or preferably about 1 mg to about 5 mg, preferably, wherein the dose (preferably, a unit dose) of the K-ATP channel blocker is about 0.1 mg, about 0.2 mg, about 0.5 mg, about 1 mg, about 1.5 mg, about 2 mg, about 4 mg or about 5 mg, or still preferably about 1 mg or about 2 mg; and preferably, the K-ATP channel blocker is glimepiride or repaglinide.

Solution 11. The pharmaceutical combination, pharmaceutical composition, or fixed dose combination formulation of any one of solutions 1-9, wherein the one or more excipients are selected from the group consisting of binders, fillers, disintegrants, lubricants, glidants, surfactants, wetting agents, antioxidants, flavoring agents, sweetening agents, coloring agents and coating agents.

Solution 12. The pharmaceutical combination, pharmaceutical composition, or fixed dose combination formulation of any one of solutions 1-11, which is a tablet.

Solution 13. The pharmaceutical combination, pharmaceutical composition, or fixed dose combination formulation of solution 12, which is a coated tablet.

Solution 14. The pharmaceutical combination, pharmaceutical composition, or fixed dose combination formulation of solution 13, wherein the coated tablet is a film-coated tablet, and the film-coating agent comprises:
film-coating substrate(s), such as hypromellose, hydroxypropyl methyl cellulose, or a mixture thereof;
optional plasticizer(s), such as polyvinyl alcohol, polyethylene glycol, propylene glycol, polysorbate, or a mixture thereof;
optional coloring agent(s), such as iron oxide red, iron oxide yellow, or a mixture thereof; optional opacifier(s), such as titanium dioxide, and
optional glidant(s).

Solution 15. The pharmaceutical combination, pharmaceutical composition, or fixed dose combination formulation of solution 14, wherein the coated tablet is a film-coated tablet, and the film-coating agent is Opadry.

Solution 16. The pharmaceutical combination, pharmaceutical composition, or fixed dose combination formulation of any one of solutions 1-15, comprising (by weight): about 1-99% of the glucokinase activator (preferably, HMS5552 or an isotope labeled analogue or a pharmaceutically acceptable salt thereof), preferably HMS5552, preferably a solid dispersion of HMS5552, preferably a solid dispersion containing HMS5552 and a polymer carrier, or preferably a solid dispersion containing about 1:1 of HMS5552 and Eudragit L100;
about 0.1-8% of repaglinide;
about 0-90% of filler(s);
about 1-25% of binder(s);
about 0-15% of disintegrant(s);
about 0.1-10% of lubricant(s);
about 0-3% of glidant(s); and
about 0-5% of coating agent(s).

Solution 17. The pharmaceutical combination, pharmaceutical composition, or fixed dose combination formulation of solution 15, comprising (by weight):
about 1 to 50% of the glucokinase activator (preferably, HMS5552 or an isotope labeled analogue or a pharmaceutically acceptable salt thereof), preferably HMS5552, preferably a solid dispersion of HMS5552, preferably a solid dispersion containing HMS5552 and a polymer carrier, or preferably a solid dispersion containing about 1:1 of HMS5552 and Eudragit L100;
about 0.1-5% of repaglinide;
about 0-90% of filler(s);
about 1-10% of binder(s);
about 1-10% of disintegrant(s);
about 0.1-5% of lubricant(s);
about 0-3% of glidant(s); and
about 0-5% of coating agent(s).

Solution 18. The pharmaceutical combination, pharmaceutical composition, or fixed dose combination formulation of solution 15, wherein the doses (preferably, unit doses) of the active ingredients are (by weight):
about 25 mg, about 50 mg, about 75 mg or about 100 mg of the glucokinase activator, or preferably HMS5552;
about 0.5 mg, about 1 mg or about 2 mg of repaglinide;
about 0-90% of filler(s);
about 1-25% of binder(s);
about 0-15% of disintegrant(s);
about 0.1-10% of lubricant(s);
about 0-3% of glidant(s); and
about 0-5% of coating agent(s).

Solution 19. The pharmaceutical combination, pharmaceutical composition, or fixed dose combination formulation (the fixed dose combination formulation is preferably a tablet of 75 mg HMS5552/1 mg repaglinide) of solution 18, comprising the components with the following amounts (by weight):
about 75 mg of HMS5552, preferably a solid dispersion of HMS5552, preferably a solid dispersion containing HMS5552 and a polymer carrier, or preferably a solid dispersion containing about 1:1 of HMS5552 and Eudragit L100;
about 1 mg of repaglinide;
about 0-95% of filler(s);
about 1-25% of binder(s);
about 1-8% of disintegrant(s);
about 0.5-3% of lubricant(s);
about 0-0.5% of glidant(s); and
about 0-5% of coating agent(s).

Solution 20. The pharmaceutical combination, pharmaceutical composition, or fixed dose combination formulation (the fixed dose combination formulation is preferably a tablet of 50 mg HMS5552/2 mg repaglinide) of solution 18, comprising the components with the following amounts (by weight):
about 50 mg of HMS5552, preferably a solid dispersion of HMS5552, preferably a solid dispersion containing HMS5552 and a polymer carrier, or preferably a solid dispersion containing about 1:1 of HMS5552 and Eudragit L100;
about 2 mg of repaglinide;
about 0-95% of filler(s);
about 1-25% of binder(s);
about 1-8% of disintegrant(s);
about 0.5-3% of lubricant(s);
about 0-0.5% of glidant(s); and
about 0-5% of coating agent(s).

Solution 21. The pharmaceutical combination, pharmaceutical composition, or fixed dose combination formulation (the fixed dose combination formulation is preferably a tablet of 25 mg HMS5552/2 mg repaglinide) of solution 18, comprising the components with the following amounts (by weight):
about 25 mg of HMS5552, preferably a solid dispersion of HMS5552, preferably a solid dispersion containing HMS5552 and a polymer carrier, or preferably a solid dispersion containing about 1:1 of HMS5552 and Eudragit L100;
about 2 mg of repaglinide;
about 0-95% of filler(s);
about 1-25% of binder(s);
about 1-8% of disintegrant(s);

about 0.5-3% of lubricant(s);
about 0-0.5% of glidant(s); and
about 0-5% of coating agent(s).

Solution 22. The pharmaceutical combination, pharmaceutical composition, or fixed dose combination formulation of solution 18, comprising about 150 mg of the solid dispersion, about 1.00 mg of repaglinide, about 79.00 mg of microcrystalline cellulose, about 7.50 mg of hydroxypropyl cellulose, about 7.50 mg of croscarmellose sodium, about 2.50 mg of sodium dodecyl sulfate, about 2.50 mg of magnesium stearate, and about 7.50 mg of Opadry, wherein the solid dispersion contains about 1:1 of HMS5552 and Eudragit L100, and contains about 75 mg of HMS5552.

Solution 23. The pharmaceutical combination, pharmaceutical composition, or fixed dose combination formulation of solution 18, comprising about 100 mg of the solid dispersion, about 2.00 mg of repaglinide, about 128.00 mg of microcrystalline cellulose, about 7.50 mg of hydroxypropyl cellulose, about 7.50 mg of croscarmellose sodium, about 2.50 mg of sodium dodecyl sulfate, about 2.50 mg of magnesium stearate, and about 7.50 mg of Opadry, wherein the solid dispersion contains about 1:1 of HMS5552 and Eudragit L100, and contains about 50 mg of HMS5552.

Solution 24. The pharmaceutical combination, pharmaceutical composition, or fixed dose combination formulation of solution 18, comprising about 50 mg of the solid dispersion, about 2.00 mg of repaglinide, about 132.0 mg of microcrystalline cellulose, about 6.00 mg of hydroxypropyl cellulose, about 6.00 mg of croscarmellose sodium, about 2.00 mg of sodium dodecyl sulfate, about 2.00 mg of magnesium stearate and about 6.00 mg of Opadry, wherein the solid dispersion contains about 1:1 of HMS5552 and Eudragit L100, and contains about 25 mg of HMS5552.

Solution 25. A method for preparing the pharmaceutical combination, pharmaceutical composition, or fixed dose combination formulation of any one of solutions 1-24, comprising incorporating the active ingredients into one or more excipients for granulation, preferably further filling the obtained granule mixture into a vial, a sachet or a capsule, or compressing it into a tablet with a desired shape; and more preferably, further coating the obtained tablet.

Solution 26. The method for preparing the pharmaceutical combination, pharmaceutical composition, or fixed dose combination formulation according to solution 25, wherein the preparation is carried out by wet granulation (high shear and/or fluidized bed), or by dry processing (direct compression or dry granulation).

Solution 27. The method for preparing the pharmaceutical combination, pharmaceutical composition, or fixed dose combination formulation according to any one of solutions 25-26, wherein the glucokinase activator is prepared in the form of a solid dispersion.

Solution 28. The method for preparing the pharmaceutical combination, pharmaceutical composition, or fixed dose combination formulation according to any one of solutions 25-27, wherein the glucokinase activator and the second or more active ingredients can also be prepared together in the form of a combination solid dispersion (that is, a solid dispersion comprising two or more active ingredients).

Solution 29. The pharmaceutical combination, pharmaceutical composition, or fixed dose combination formulation of any one of solutions 1-24, which is used to prevent, slow the progression of, delay, or treat one or more metabolic disorders selected from the group consisting of: type I diabetes, type II diabetes, maturity-onset diabetes of the young (MODY), impaired glucose tolerance, impaired fasting blood glucose, hyperglycemia, postprandial hyperglycemia, overweight, obesity, hypertension, insulin resistance, diseases associated with islet dysfunction and/or metabolic syndrome; or improve blood glucose control and/or reduce fasting plasma glucose, postprandial plasma glucose and/or glycosylated hemoglobin HbA1c; or prevent, slow, delay, or reverse complications of diabetes mellitus.

Solution 30. A method for preventing, slowing the progression of, delaying, or treating one or more metabolic disorders selected from the group consisting of: type I diabetes, type II diabetes, maturity-onset diabetes of the young (MODY), impaired glucose tolerance, impaired fasting blood glucose, hyperglycemia, postprandial hyperglycemia, overweight, obesity, hypertension, insulin resistance, diseases associated with islet dysfunction and/or metabolic syndrome; or improving blood glucose control and/or reducing fasting plasma glucose, postprandial plasma glucose and/or glycosylated hemoglobin HbA1c; or preventing, slowing, delaying, or reversing complications of diabetes mellitus, comprising administering to a subject a therapeutically effective amount of the pharmaceutical combination, pharmaceutical composition or fixed dose combination formulation of any one of solutions 1-24.

Solution 31. Use of the pharmaceutical combination, pharmaceutical composition or fixed dose combination formulation of any one of solutions 1-24 in the manufacture of a medicament for preventing, slowing the progression of, delaying, or treating one or more metabolic disorders selected from the group consisting of: type I diabetes, type II diabetes, maturity-onset diabetes of the young (MODY), impaired glucose tolerance, impaired fasting blood glucose, hyperglycemia, postprandial hyperglycemia, overweight, obesity, hypertension, insulin resistance, diseases associated with islet dysfunction and/or metabolic syndrome; or improving blood glucose control and/or reducing fasting plasma glucose, postprandial plasma glucose and/or glycosylated hemoglobin HbA1c.

The following examples further describe and illustrate embodiments within the scope of the present disclosure. However, the present invention is not limited to the examples, and various modifications and substitutions made on the basis of the technology disclosed herein are within the protection scope of the present invention.

EXAMPLES

Preparation of the Combination Tablet of the Glucokinase Activator

The chemicals used in the present disclosure can be purchased from companies such as Shin-Etsu Japan, Evonik Germany, J.T. Baker US, SCR China, Ashland US, FMC US, JRS Germany, Colorcon US, Capsugel, BASF, Zhenxing China, and the like. A producing equipment, analytical testing instrument and the like can be purchased from companies such as Sartorius, Nikon, Sympatec, Bruker, Gea Niro, Korsch, Erweka, Agilent, Quadro Engineering, Canada; Waters, US; TA, US; SOTAX, Switzerland; Mettler Toledo Instrument Newark, Del.

I. Preparation of the Solid Dispersion of the Glucokinase Activator 1.1 Preparation of the Solution of the Solid Dispersion Used for Spray Drying Example 1A (Weight Ratio of Active Ingredients to Polymer Carriers is 1:9)

6.75 g Eudragit L100 (Evonik Germany) was weighed, and added to anhydrous ethanol (J.T.Baker) under stirring.

After it was completely dissolved, 0.75 g of the compound HMS5552 was added. Stirring was continued after adding sufficient amount of anhydrous ethanol to obtain 50 ml solution.

Example 2A (Weight Ratio of Active Ingredients to Polymer Carriers is 3:7)

5.25 g Eudragit L100 (Evonik Germany) was weighed, and added to anhydrous ethanol (J.T.Baker) under stirring. After it was completely dissolved, 2.25 g of the compound HMS5552 was added. Stirring was continued after adding sufficient amount of anhydrous ethanol to obtain 50 ml solution.

Example 3A (Weight Ratio of Active Ingredients to Polymer Carriers is 5:5)

3.75 g Eudragit L100 (Evonik Germany) was weighed, and added to anhydrous ethanol (J.T.Baker) under stirring. After it was completely dissolved, 3.75 g of the compound HMS5552 was added. Stirring was continued after adding sufficient amount of anhydrous ethanol to obtain 50 ml solution.

Example 4A (Weight Ratio of Active Ingredients to Polymer Carriers is 7:3)

2.25 g Eudragit L100 (Evonik Germany) was weighed, and added to anhydrous ethanol (J.T.Baker) under stirring. After it was completely dissolved, 5.25 g of the compound HMS5552 was added. Stirring was continued after adding sufficient amount of anhydrous ethanol to obtain 50 ml solution.

Example 5A (Weight Ratio of Active Ingredients to Polymer Carriers is 8:2)

1.5 g Eudragit L100 (Evonik Germany) was weighed, and added to anhydrous ethanol (J.T.Baker) under stirring. After it was completely dissolved, 6 g of the compound HMS5552 was added. Stirring was continued after adding sufficient amount of anhydrous ethanol to obtain 50 ml solution.

Example 6A (Weight Ratio of Active Ingredients to Polymer Carriers is 9:1)

0.75 g Eudragit L100 (Evonik Germany) was weighed, and added to anhydrous ethanol (J.T.Baker) under stirring. After it was completely dissolved, 6.75 g of the compound HMS5552 was added. Stirring was continued after adding sufficient amount of anhydrous ethanol to obtain 50 ml solution.

Example 7A (Weight Ratio of Active Ingredients to Polymer Carriers is 6:4)

3.0 g Eudragit L100 (Evonik Germany) was weighed, and added to anhydrous ethanol (J.T.Baker) under stirring. After it was completely dissolved, 4.5 g of the compound HMS5552 was added. Stirring was continued after adding sufficient amount of anhydrous ethanol to obtain 50 ml solution.

Example 8A (Weight Ratio of Active Ingredients to Polymer Carriers is 4:6)

4.5 g Eudragit L100 (Evonik Germany) was weighed, and added to anhydrous ethanol (J.T.Baker) under stirring. After it was completely dissolved, 3.0 g of the compound HMS5552 was added. Stirring was continued after adding sufficient amount of anhydrous ethanol to obtain 50 ml solution.

Example 9A (Weight Ratio of Active Ingredients to Polymer Carriers is 5:5)

187.5 g Eudragit L100 (Evonik Germany) was weighed, and added to anhydrous ethanol (Zhenxing China). After it was completely dissolved, 187.5 g of the compound HMS5552 was added. Stirring was continued after adding sufficient amount of anhydrous ethanol to obtain 2500 ml solution.

1.2 Preparation of the solid dispersion of the glucokinase activator

The solid dispersion of the glucokinase activator was prepared by spray drying the solution prepared above. The numbering of the obtained solid dispersion corresponds to the numbering of the above examples. The spray drying devices that are suitable for the present disclosure include, but are not limited to, the spray drying devices produced by Niro GEA Process Engineering Inc., Buchi Labortechnik AG, ProCept and SPX ANHYDROUS companies. The spray drying can be performed by selecting an appropriate inlet air temperature of dry gas, inlet amount, feed rate, and atomization pressure, so that the droplets are sufficiently dried as they reach the device wall. This can make sure that the dried droplets are essentially solid and in a form of a fine powder, which will not stick to the wall, and is not difficult to collect in the cyclone. The resulting powder is subjected to a secondary drying to make sure the product meets quality requirement.

Description of the Production Process for the Preparation of the Solid Dispersion of the Glucokinase Activator by Spray Drying The solid dispersions were prepared by the spray drying the solution prepared in the above Examples 1A-8A, wherein the inlet air temperature of the spray dryer was 90-150° C., the flow rate of the inlet air was 0.3-0.5 m$^3$/min, the flow rate of the air flow was 15-30 L/min, and the spray rate of above solutions were 5-7 mL/min. Solid dispersions 1-8 were obtained by spray drying.

The solid dispersion was prepared by spray drying the solution prepared in the above Example 9A, wherein the inlet air temperature of the spray dryer was 90-150° C., the flow rate of the inlet air was 20-30 kg/h, the flow rate of the air flow was 3-30 kg/h, and the spray rate of above solutions were 5-200 mL/min. Solid dispersion 9 was obtained by spray drying.

Solid dispersions 1-9 were prepared according to the process described above, wherein:
mass percent of the compound HMS5552 in solid dispersion 1 was 10%; mass percent of the compound HMS5552 in solid dispersion 2 was 30%; mass percent of the compound HMS5552 in solid dispersion 3 was 50%; mass percent of the compound HMS5552 in solid dispersion 4 was 70%; mass percent of the compound HMS5552 in solid dispersion 5 was 80%; mass percent of the compound HMS5552 in solid dispersion 6 was 90%; mass percent of the compound HMS5552 in solid dispersion 7 was 60%; mass percent of the compound HMS5552 in solid dispersion 8 was 40%; and mass percent of the compound HMS5552 in solid dispersion 9 was 50%.

II. Preparation of the Combination Tablet 2.1 Preparation of the Combination Tablet by High-Shear Wet Granulation The HMS5552 solid dispersion prepared according to the above preparation examples of the solid dispersion of the glucokinase activator and the partner drug were added into a high-shear wet granulator. The filler (e.g., microcrystalline cellulose, silicified microcrystalline cellulose, or lactose) and disintegrant (e.g., croscarmellose sodium, crospovidone, or sodium starch glycolate) were added. A part of the binder powder was added and mixed for 5 minutes with high-shear stirring. A prepared solution of the binder (e.g., hydroxypropyl cellulose, polyvinylpyrrolidone or hydroxypropyl methyl cellulose) was added to the above dry mixture under high-shear stirring for 1 to 6 minutes for granulation. Wet granules are sized on a Comil mill to obtain wet granules of suitable size. The wet granules were dried with a tray in an oven at about 60° C. or in a fluidized bed dryer (with the inlet air temperature of 40-60° C.) for 20-40 minutes. Then, the dried material was ground using a grinder to obtain granules of suitable size. After grinding, the microcrystalline cellulose or silicified microcrystalline cellulose (for the filler comprising an extragranular part) and the disintegrant (e.g., croscarmellose sodium, crospovidone, or sodium starch glycolate) were added to the granules and the mixture was mixed in a barrel mixer. Then, the lubricant (magnesium stearate or sodium stearyl fumarate) and/or optional glidant (micronized silica gel) were added to the mixture and mixed well additionally. The lubricated mixture was compressed with a rotary tablet press to obtain tablets (plain tablets, uncoated tablet cores) of different tablet weights and tablet shapes corresponding to different strengths. Optionally, the obtained tablets were film-coated with Opadry® II, and the weight increased by about 3%, thereby obtaining film-coated tablets.

Example 1B A Combination Tablet of HMS5552+Glimepiride (Dose Strength: 50 mg/1 mg)

| Formula composition | Unit formula amount/mg | % (w/w) |
|---|---|---|
| Glimepiride | 1.00 | 0.40 |
| HMS5552 solid dispersion* | 100.00 | 40.00 |
| Microcrystalline cellulose | 129.00 | 51.60 |
| Hydroxypropyl cellulose | 7.50 | 3.00 |
| Croscarmellose sodium | 7.50 | 3.00 |
| Sodium dodecyl sulfate | 2.50 | 1.00 |
| Magnesium stearate | 2.50 | 1.00 |
| Total weight of a tablet core | 250.00 | 100.00 |
| Opadry | 7.50 | 3.00 |
| Total weight of a coated tablet | 257.50 | — |

*100.00 mg of the HMS5552 solid dispersion contained 50 mg of HMS5552.

Example 2B A Combination Tablet of HMS5552+Glimepiride (Dose Strength: 75 mg/1 mg)

| Formula composition | Unit formula amount/mg | % (w/w) |
|---|---|---|
| Glimepiride | 1.00 | 0.40 |
| HMS5552 solid dispersion* | 150.00 | 60.00 |
| Microcrystalline cellulose | 79.00 | 31.60 |
| Hydroxypropyl cellulose | 7.50 | 3.00 |
| Croscarmellose sodium | 7.50 | 3.00 |
| Sodium dodecyl sulfate | 2.50 | 1.00 |
| Magnesium stearate | 2.50 | 1.00 |
| Total weight of a tablet core | 250.00 | 100.00 |
| Opadry | 7.50 | 3.00 |
| Total weight of a coated tablet | 257.50 | — |

*150.00 mg of the HMS5552 solid dispersion contained 75 mg of HMS5552.

Example 3B A Combination Tablet of HMS5552+Glimepiride (Dose Strength: 100 mg/1 mg

| Formula composition | Unit formula amount/mg | % (w/w) |
|---|---|---|
| Glimepiride | 1.00 | 0.40 |
| HMS5552 solid dispersion* | 200.00 | 80.00 |
| Microcrystalline cellulose | 29.00 | 11.60 |
| Hydroxypropyl cellulose | 7.50 | 3.00 |
| Croscarmellose sodium | 7.50 | 3.00 |
| Sodium dodecyl sulfate | 2.50 | 1.00 |
| Magnesium stearate | 2.50 | 1.00 |
| Total weight of a tablet core | 250.00 | 100.00 |
| Opadry | 7.50 | 3.00 |
| Total weight of a coated tablet | 257.50 | — |

*200.00 mg of the HMS5552 solid dispersion contained 100 mg of HMS5552.

Example 4B A Combination Tablet of HMS5552+Glimepiride (Dose Strength: 50 mg/2 mg)

| Formula composition | Unit formula amount/mg | % (w/w) |
|---|---|---|
| Glimepiride | 2.00 | 0.80 |
| HMS5552 solid dispersion* | 100.00 | 40.00 |
| Microcrystalline cellulose | 128.00 | 51.20 |
| Hydroxypropyl cellulose | 7.50 | 3.00 |
| Croscarmellose sodium | 7.50 | 3.00 |
| Sodium dodecyl sulfate | 2.50 | 1.00 |
| Magnesium stearate | 2.50 | 1.00 |
| Total weight of a tablet core | 250.00 | 100.00 |
| Opadry | 7.50 | 3.00 |
| Total weight of a coated tablet | 257.50 | — |

*100.00 mg of the HMS5552 solid dispersion contained 50 mg of HMS5552

Example 5B A Combination Tablet of HMS5552+Glimepiride (Dose Strength: 75 mg/2 mg)

| Formula composition | Unit formula amount/mg | % (w/w) |
|---|---|---|
| Glimepiride | 2.00 | 0.80 |
| HMS5552 solid dispersion* | 150.00 | 60.00 |
| Microcrystalline cellulose | 78.00 | 31.20 |
| Hydroxypropyl cellulose | 7.50 | 3.00 |
| Croscarmellose sodium | 7.50 | 3.00 |
| Sodium dodecyl sulfate | 2.50 | 1.00 |
| Magnesium stearate | 2.50 | 1.00 |
| Total weight of a tablet core | 250.00 | 100.00 |
| Opadry | 7.50 | 3.00 |
| Total weight of a coated tablet | 257.50 | — |

*150.00 mg of the HMS5552 solid dispersion contained 75 mg of HMS5552.

Example 6B A Combination Tablet of HMS5552+Repaglinide (Dose Strength: 75 mg/1 mg)

| Formula composition | Unit formula amount/mg | % (w/w) |
|---|---|---|
| Repaglinide | 1.00 | 0.40 |
| HMS5552 solid dispersion* | 150.00 | 60.00 |
| Microcrystalline cellulose | 79.00 | 31.60 |
| Hydroxypropyl cellulose | 7.50 | 3.00 |
| Croscarmellose sodium | 7.50 | 3.00 |
| Sodium dodecyl sulfate | 2.50 | 1.00 |
| Magnesium stearate | 2.50 | 1.00 |
| Total weight of a tablet core | 250.00 | 100.00 |
| Opadry | 7.50 | 3.00 |
| Total weight of a coated tablet | 257.50 | — |

*150.00 mg of the HMS5552 solid dispersion contained 75 mg of HMS5552.

Example 7B A Combination Tablet of HMS5552+Repaglinide (Dose Strength: 50 mg/2 mg)

| Formula composition | Unit formula amount/mg | % (w/w) |
|---|---|---|
| Repaglinide | 2.00 | 0.80 |
| HMS5552 solid dispersion* | 100.00 | 40.00 |
| Microcrystalline cellulose | 128.00 | 51.20 |
| Hydroxypropyl cellulose | 7.50 | 3.00 |
| Croscarmellose sodium | 7.50 | 3.00 |
| Sodium dodecyl sulfate | 2.50 | 1.00 |
| Magnesium stearate | 2.50 | 1.00 |
| Total weight of a tablet core | 250.00 | 100.00 |
| Opadry | 7.50 | 3.00 |
| Total weight of a coated tablet | 257.50 | — |

*100.00 mg of the HMS5552 solid dispersion contained 50 mg of HMS5552.

2.2 Preparation of the Combination Tablet by Fluidized Bed Wet Granulation

The HMS5552 solid dispersion prepared according to the above preparation examples of the solid dispersion of the glucokinase activator and the partner drug were added into a fluidized bed granulator. The optional filler (e.g., microcrystalline cellulose) was added. The prepared solution of the binder (e.g., polyvinylpyrrolidone) was sprayed into the mixture in the fluidized bed during 20 to 60 minutes for granulation, and then drying was continued in a fluidized bed dryer (with the inlet air temperature of 40-60° C.). Then, the dried material was ground using a grinder to obtain granules of suitable size. After grinding, the microcrystalline cellulose or silicified microcrystalline cellulose (for the formulation comprising an extragranular filler) was added to the granules, and the mixture was mixed in a barrel mixer. Then, the lubricant (magnesium stearate) and/or optional glidant (micronized silica gel) were added to the mixture and mixed well additionally. The lubricated mixture was compressed with a rotary tablet press to obtain tablets (plain tablets, uncoated tablet cores) of different tablet weights and tablet shapes corresponding to different strengths. Optionally, the obtained tablets were film-coated according to the above preparation examples of the solid dispersion of the glucokinase activator, and the weight increased by about 3%, thereby obtaining film-coated tablets.

2.3 Preparation of the Combination Tablet by Dry Rolling Granulation

The HMS5552 solid dispersion prepared according to the above preparation examples of the solid dispersion of the glucokinase activator and the partner drug were added into a mixing tank. The filler (e.g., microcrystalline cellulose) and the binder (e.g., hydroxypropyl cellulose) were added and mixed well. Then, the mixture was rolled by a roller compaction granulator, and the obtained bar was crushed and sized by a crusher to obtain granules of suitable size. After grinding, the optional microcrystalline cellulose or silicified microcrystalline cellulose (for the filler comprising an extragranular part) and the disintegrant (e.g., croscarmellose sodium) were added to the granules, and the mixture was mixed in a barrel mixer. Then, the lubricant (magnesium stearate or sodium stearyl fumarate) and/or optional glidant (micronized silica gel) were added to the mixture and mixed well additionally. The lubricated mixture was compressed with a rotary tablet press to obtain tablets (plain tablets, uncoated tablet cores) of different tablet weights and tablet shapes corresponding to different strengths. Optionally, the obtained tablets were film-coated with Opadry® II, and the weight increased by about 3%, thereby obtaining film-coated tablets.

Example 8B A Combination Tablet of HMS5552+Repaglinide (Dose Strength: 25 mg/2 mg)

| Formula composition | Unit formula amount/mg | % (w/w) |
|---|---|---|
| Repaglinide | 2.00 | 1.00 |
| HMS5552 solid dispersion* | 50.00 | 25.0 |
| Microcrystalline cellulose | 132.00 | 66.0 |
| Hydroxypropyl cellulose | 6.00 | 3.00 |
| Croscarmellose sodium | 6.00 | 3.00 |
| Sodium dodecyl sulfate | 2.00 | 1.00 |
| Magnesium stearate | 2.00 | 1.00 |
| Total weight of a tablet core | 200 | 100.00 |
| Opadry | 6.00 | 3.00 |
| Total weight of a coated tablet | 206.00 | — |

*50.00 mg of the HMS5552 solid dispersion contained 25 mg of HMS5552.

2.4 Preparation of the Combination Tablet by Direct Compression of the Powder Mixture The HMS5552 solid dispersion prepared according to the above preparation examples of the solid dispersion of the glucokinase activator and the partner drug were premixed uniformly according to the principle of geometric progression, and then added to a mixing tank. The filler (e.g., microcrystalline cellulose), the disintegrant (e.g., croscarmellose sodium) and optional glidant (micronized silica gel) were added to the granules and mixed in a barrel mixer. Then, the lubricant (magnesium stearate or sodium stearyl fumarate) was added to the mixture and mixed well additionally. The lubricated mixture was compressed with a rotary tablet press to obtain tablets (plain tablets, uncoated tablet cores) of different tablet weights and tablet shapes corresponding to different strengths. Optionally, the obtained tablets were film-coated with Opadry® II, and the weight increased by about 3%, thereby obtaining film-coated tablets.

The formula composition of the combination tablet described in the above preparation process was:

Example 9B A Combination Tablet of
HMS5552+Glimepiride (Dose Strength: 25 mg/2 mg)

| Formula composition | Unit formula amount/mg | % (w/w) |
|---|---|---|
| Glimepiride | 2.00 | 1.00 |
| HMS5552 solid dispersion* | 50.00 | 25.00 |
| Microcrystalline cellulose | 136.00 | 68.00 |
| Hydroxypropyl cellulose | 4.00 | 2.00 |
| Croscarmellose sodium | 4.00 | 2.00 |
| Sodium dodecyl sulfate | 2.00 | 1.00 |
| Magnesium stearate | 2.00 | 1.00 |
| Total weight of a tablet core | 200.00 | 100.00 |
| Opadry | 6.00 | 3.00 |
| Total weight of a coated tablet | 206.00 | — |

*50.00 mg of the HMS5552 solid dispersion contained 25 mg of HMS5552.

III. Dissolution Test In Vitro of the Combination Formulation Comprising the Glucokinase Activator The dissolution rate of the tablet was tested by the paddle method of the Chinese Pharmacopoeia (2015 edition). The dissolution of HMS5552 and another partner drug in the medium of pH 6.8 was tested, respectively. At 5 minutes, 15 minutes, 30 minutes, 45 minutes, and 60 minutes, respectively, 5 ml of samples were taken for HPLC analysis.

According to the above test method, several tablets of above-mentioned fixed dose strengths and their corresponding single tablets were tested for their dissolution, and the results were shown below.

TABLE 1

The dissolution results of the fixed dose combination tablets prepared in Example 7B

| Time point | Dissolution rate (%) | | | | |
|---|---|---|---|---|---|
| | 5 min | 15 min | 30 min | 45 min | 60 min |
| Example 7B—HMS5552, 50 mg | 68.4 | 88.6 | 93.8 | 95.4 | 97.4 |
| Example 7B—repaglinide, 2 mg | 53.7 | 73.9 | 82.4 | 86.9 | 90.0 |

TABLE 2

The dissolution results of the fixed dose combination tablets prepared in Example 8B

| Time point | Dissolution rate (%) | | | | |
|---|---|---|---|---|---|
| | 5 min | 15 min | 30 min | 45 min | 60 min |
| Example 8B—HMS5552, 25 mg | 32.7 | 77.6 | 86.6 | 89.1 | 91.5 |
| Example 8B—repaglinide, 2 mg | 25.7 | 62.4 | 74.3 | 79.9 | 83.9 |

It can be seen from the above dissolution results of the fixed dose combination formulations that the dissolution of the fixed dose combination formulations disclosed herein meets the requirements of a fast-release formulation.

IV. Physical Properties of the Combination Formulations Containing the Glucokinase Activator According to the relevant instruments and methods described in the Pharmacopoeia, the physical properties of several tablets of above-mentioned fixed-dose strengths were tested. The results were described below.

TABLE 3

Physical properties of the fixed dose combination tablet cores prepared in different examples

| Item | A combination tablet of HMS5552/glimepiride, mg | | | | | |
|---|---|---|---|---|---|---|
| Dose strength | 50/1 | 75/1 | 100/1 | 50/2 | 75/2 | 25/2 |
| Corresponding Example | 1B | 2B | 3B | 4B | 5B | 9B |
| Tablet shape | Round biconvex | Round biconvex | Round biconvex | Round biconvex | Round biconvex | Round biconvex |
| Tablet core size/mm | 9.00 | 9.00 | 9.00 | 9.00 | 9.00 | 9.00 |
| Colour | white | white | white | white | white | white |
| Weight/mg | 250 | 250 | 250 | 250 | 250 | 200 |
| Hardness/kp (average value) | ≥7 | ≥7 | ≥7 | ≥7 | ≥7 | ≥7 |

TABLE 3-continued

Physical properties of the fixed dose combination tablet cores prepared in different examples

| Item | A combination tablet of HMS5552/glimepiride, mg | | | | | |
|---|---|---|---|---|---|---|
| Disintegration time/minute | ≤10 | ≤10 | ≤10 | ≤10 | ≤10 | ≤10 |
| Fragility/% | ≤0.5 | ≤0.5 | ≤0.5 | ≤0.5 | ≤0.5 | ≤0.5 |

TABLE 4

Physical properties of the fixed dose combination tablet cores prepared in different examples

| Item | A combination tablet of HMS5552/repaglinide, mg | | |
|---|---|---|---|
| Dose strength | 75/1 | 50/2 | 25/2 |
| Corresponding Example | 6B | 7B | 8B |
| Tablet shape | Round biconvex | Round biconvex | Round biconvex |
| Tablet core size/mm | 9.00 | 9.00 | 9.00 |
| Colour | white | white | white |
| Weight/mg | 300 | 300 | 400 |
| Hardness/kp (average value) | ≥10 | ≥10 | ≥10 |
| Disintegration time/minute | ≤10 | ≤10 | ≤10 |
| Fragility/% | ≤0.5 | ≤0.5 | ≤0.5 |

V. Study on Pharmacodynamics of the Combination Formulations Comprising the Glucokinase Activator Example 1C Study on the Effect of the Combination of the Glucokinase Activator and the Partner Drug on Glucose/Sucrose Tolerance in Normal Mice Normal male C57BL/6J mice, after being fasted for 6 hours, were orally administered solvent control, 1 mg/kg of repaglinide, or a combination of 10 mg/kg of HMS5552 and 1 mg/kg of repaglinide, respectively; and after 1 hour, were orally given 2 g/kg of glucose. Blood was taken from the tail vein before being administered (−60 minutes), before being given the glucose (0 minutes), and at 15, 30, 60, and 120 minutes after being given the glucose, and the glucose content in the whole blood was determined. The area under the curve for blood glucose between 0 and 120 minutes (AUC0-120 min, mmol/L*min) was analyzed and compared with that of the solvent control group. The results showed that the hypoglycemic effect of the combination of 10 mg/kg of HMS5552 and 1 mg/kg of repaglinide is significantly better than that of the monotherapy of 1 mg/kg of repaglinide, with statistically significant difference of P<0.001.

A sulfonylurea hypoglycemic agent and a glinide hypoglycemic agent are K-ATP channel blockers, which reduce blood glucose by promoting the secretion of insulin by islet β cells, and are widely used clinically to treat type 2 diabetes. HMS5552, a novel glucokinase activator, can improve pancreatic islet function in patients with type 2 diabetes, promote the secretion of incretin, reduce insulin resistance, and has dual therapeutic effects of reducing fasting and postprandial blood glucose. For type 2 diabetic patients whose blood glucose control by a sulfonylurea hypoglycemic agent or a glinide hypoglycemic agent fails, the combination of a sulfonylurea hypoglycemic agent or a glinide hypoglycemic agent and HMS5552 has better efficacy of blood glucose control and reduces the risk of diabetes complications.

The above study on the effectiveness of HMS5552 combined with the existing oral diabetes drug shows that the combined use can improve the efficacy of HMS5552 or existing hypoglycemic drugs, reduce safety risks, and improve medical effects. Oral fixed dose combination formulations developed with HMS5552 and existing oral diabetes drugs are currently the most promising combination drugs for diabetes treatment to solve the above clinical needs.

What is claimed is:

1. A fixed dose combination formulation, comprising:
   (a) a glucokinase activator, which is a compound represented by the following formulae, or a pharmaceutically acceptable salt, an isotope labeled analogue, a crystalline form, a hydrate, a solvate, or a diastereomeric or enantiomeric form thereof,

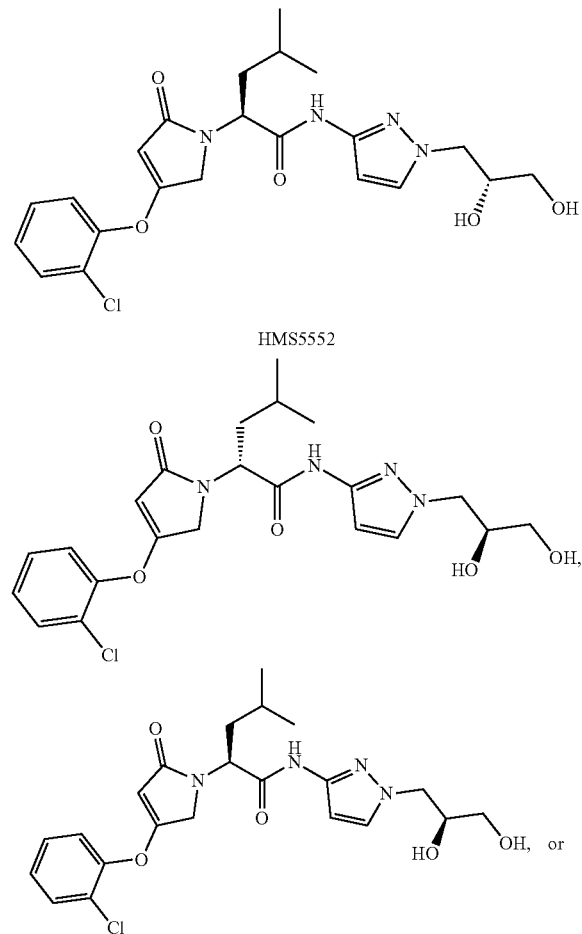

-continued

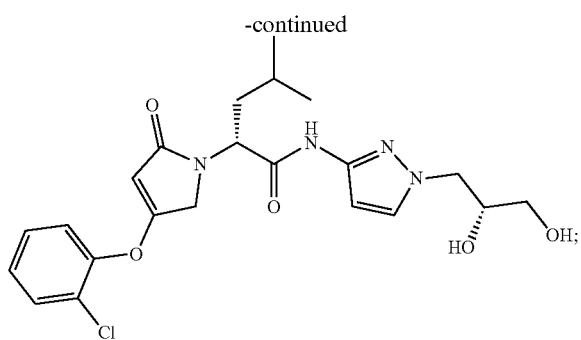

(b) a K-ATP channel blocker; and
(c) one or more excipients, wherein said K-ATP channel blocker is repaglinide, and wherein the glucokinase activator is about 1-99% by weight; and the K-ATP channel blocker is about 0.1-15% by weight.

2. The fixed dose combination formulation of claim 1, wherein the weight ratio of the glucokinase activator to the K-ATP channel blocker is about 200:1 to 10:1.

3. The fixed dose combination formulation of claim 1, wherein the glucokinase activator is the compound HMS5552 represented by the following formula, or an isotope labeled analogue or a pharmaceutically acceptable salt thereof,

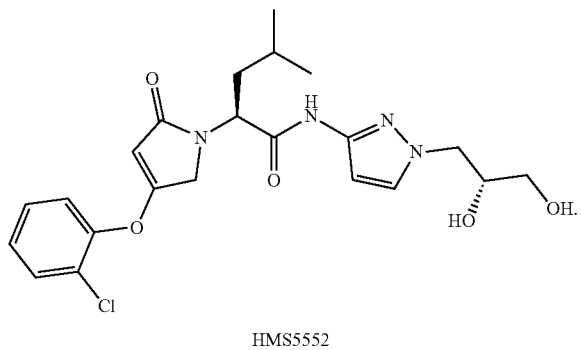 [SMILES: CC(C)C[C@@H](C(=O)Nc1ccn(C[C@@H](O)CO)n1)N1CC(Oc2ccccc2Cl)=CC1=O]

HMS5552

4. The fixed dose combination formulation of claim 1, wherein the glucokinase activator is in the form of a solid dispersion containing a polymer carrier.

5. The fixed dose combination formulation of claim 4, wherein the weight ratio of the glucokinase activator to the polymer carrier is about 1:10 to 10:1, about 1:9 to 9:1, about 1:4 to 4:1, about 3:7 to 7:3, about 2:3 to 3:2, about 3:4 to 4:3, about 4:5 to 5:4, about 5:6 to 6:5, about 1:1, about 2:3, about 3:4, about 4:5 or about 5:6.

6. The fixed dose combination formulation of claim 1, wherein the glucokinase activator is present in a dose ranging from about 1 mg to about 200 mg.

7. The fixed dose combination formulation of claim 1, wherein the K-ATP channel blocker is present in a dose ranging from about 0.1 mg to about 10 mg.

8. The fixed dose combination formulation of claim 1, wherein the one or more excipients are selected from the group consisting of binders, fillers, disintegrants, lubricants, glidants, surfactants, wetting agents, antioxidants, flavoring agents, sweetening agents, coloring agents and coating agents.

9. The fixed dose combination formulation of claim 8, wherein the binder is selected from the group consisting of polyvinylpyrrolidone, hydroxypropyl cellulose and hydroxypropyl methyl cellulose; the filler is selected from the group consisting of microcrystalline cellulose, silicified microcrystalline cellulose, lactose, calcium dihydrogen phosphate, mannitol, corn starch and pregelatinized starch; the disintegrant is selected from the group consisting of croscarmellose sodium, crospovidone and sodium starch glycolate; the lubricant is selected from the group consisting of magnesium stearate and sodium stearyl fumarate; and the glidant is selected from the group consisting of colloidal silicon dioxide and talc.

10. The fixed dose combination formulation of claim 1, which is a tablet.

11. The fixed dose combination formulation of claim 10, which is a coated tablet.

12. The fixed dose combination formulation of claim 11, wherein the coated tablet is a film-coated tablet, wherein the film-coating agent comprises:
film-coating substrate(s), which is hypromellose, hydroxypropyl methyl cellulose, or a mixture thereof;
optional plasticizer(s), which is polyvinyl alcohol, polyethylene glycol, propylene glycol, polysorbate, or a mixture thereof;
optional coloring agent(s), which is iron oxide red, iron oxide yellow, or a mixture thereof;
optional opacifier(s), which is titanium dioxide, and
optional glidant(s).

13. The fixed dose combination formulation of claim 11, wherein the coated tablet is a film-coated tablet, and the film-coating agent is Opadry.

14. The fixed dose combination formulation of claim 1, comprising by weight:
about 1-99% of a solid dispersion containing HMS5552 and a polymer carrier;
about 0.1-15% of the K-ATP channel blocker;
about 0-80% of filler(s);
about 1-25% of binder(s);
about 0-15% of disintegrant(s);
about 0.1-10% of lubricant(s); and
about 0-3% of glidant(s).

15. The fixed dose combination formulation of claim 1, comprising by weight:
about 75 mg of HMS5552 in a solid dispersion containing about 1:1 of HMS5552 and Eudragit L100;
about 1 mg of repaglinide;
about 0-95% of filler(s);
about 1-25% of binder(s);
about 1-8% of disintegrant(s);
about 0.5-3% of lubricant(s); and
about 0-0.5% of glidant(s).

16. The fixed dose combination formulation of claim 1, comprising by weight:
about 50 mg of HMS5552 in a solid dispersion containing about 1:1 of HMS5552 and Eudragit L100;
about 2 mg of repaglinide;
about 0-95% of filler(s);
about 1-25% of binder(s);
about 1-8% of disintegrant(s);
about 0.5-3% of lubricant(s); and
about 0-0.5% of glidant(s).

17. The fixed dose combination formulation of claim 1, comprising by weight:
about 25 mg of HMS5552 in a solid dispersion containing about 1:1 of HMS5552 and Eudragit L100;
about 2 mg of repaglinide;
about 0-95% of filler(s);
about 1-25% of binder(s);

about 1-8% of disintegrant(s);
about 0.5-3% of lubricant(s); and
about 0-0.5% of glidant(s).

18. The fixed dose combination formulation of claim 1, comprising about 150 mg of a solid dispersion that contains about 1:1 of HMS5552 and Eudragit L100, about 1.00 mg of repaglinide, about 79.00 mg of microcrystalline cellulose, about 7.50 mg of hydroxypropyl cellulose, about 7.50 mg of croscarmellose sodium, about 2.50 mg of sodium dodecyl sulfate, about 2.50 mg of magnesium stearate, and about 7.50 mg of Opadry.

19. The fixed dose combination formulation of claim 1, comprising about 100 mg of a solid dispersion that contains about 1:1 of HMS5552 and Eudragit L100, about 2.00 mg of repaglinide, about 128.00 mg of microcrystalline cellulose, about 7.50 mg of hydroxypropyl cellulose, about 7.50 mg of croscarmellose sodium, about 2.50 mg of sodium dodecyl sulfate, about 2.50 mg of magnesium stearate, and about 7.50 mg of Opadry.

20. The fixed dose combination formulation of claim 1, comprising about 50 mg of a solid dispersion that contains about 1:1 of HMS5552 and Eudragit L100, about 2.00 mg of repaglinide, about 132.00 mg of microcrystalline cellulose, about 6.00 mg of hydroxypropyl cellulose, about 6.00 mg of croscarmellose sodium, about 2.00 mg of sodium dodecyl sulfate, about 2.00 mg of magnesium stearate, and about 6.00 mg of Opadry.

21. A method for preparing the fixed dose combination formulation of claim 1, comprising incorporating the active ingredients into one or more excipients for granulation, optionally further filling the obtained granule mixture into a vial, a sachet or a capsule, or compressing it into a tablet with a desired shape; and optionally further coating the obtained tablet.

22. The fixed dose combination formulation of claim 4, wherein the polymer carrier is Eudragit.

23. The fixed dose combination formulation of claim 22, wherein the polymer carrier is Eudragit L100.

* * * * *